US012806267B2

(12) United States Patent
Ye et al.

(10) Patent No.: US 12,806,267 B2
(45) Date of Patent: Nov. 24, 2026

(54) METHOD OF TREATING AN AUTOIMMUNE DISEASE WITH ANTAGONISTIC CD40 MONOCLONAL ANTIBODIES

(71) Applicant: BRISTOL-MYERS SQUIBB COMPANY, Princeton, NJ (US)

(72) Inventors: Ying Ye, Branchburg, NJ (US); Urvi Aras, Kendall Park, NJ (US); Nidhi Sharda, West Windsor, NJ (US); Mary Struthers, Edison, NJ (US); Karen Price, Sauquoit, NY (US); Ihab Girgis, Princeton, NJ (US); Aberra Fura, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 629 days.

(21) Appl. No.: 18/042,553

(22) PCT Filed: Aug. 25, 2021

(86) PCT No.: PCT/US2021/047610

§ 371 (c)(1), (2) Date: Feb. 22, 2023

(87) PCT Pub. No.: WO2022/046942

PCT Pub. Date: Mar. 3, 2022

(65) Prior Publication Data

US 2023/0331860 A1 Oct. 19, 2023

Related U.S. Application Data

(60) Provisional application No. 63/070,209, filed on Aug. 25, 2020.

(51) Int. Cl.

| | |
|---|---|
| ***A61P 37/06*** | (2006.01) |
| ***A61K 39/395*** | (2006.01) |
| *A61K 39/00* | (2006.01) |
| *C07K 14/705* | (2006.01) |
| *C07K 16/28* | (2006.01) |

(52) U.S. Cl.

CPC .......... *A61K 39/3955* (2013.01); *A61P 37/06* (2018.01); *A61K 2039/545* (2013.01); *C07K 14/70578* (2013.01); *C07K 16/2878* (2013.01)

(58) Field of Classification Search

CPC ................ A61K 39/3955; A61P 37/06; C07K 14/70578; C07K 16/2878

See application file for complete search history.

(56) References Cited

U.S. PATENT DOCUMENTS

| | | | | |
|---|---|---|---|---|
| 5,530,101 | A | 6/1996 | Queen et al. | |
| 5,585,089 | A | 12/1996 | Queen et al. | |
| 5,693,762 | A | 12/1997 | Queen et al. | |
| 6,180,370 | B1 | 1/2001 | Queen et al. | |
| 6,687,673 | B2 | 2/2004 | Mann | |
| 6,737,056 | B1 | 5/2004 | Presta | |
| 7,183,387 | B1 | 2/2007 | Presta | |
| 8,637,032 | B2 | 1/2014 | Long et al. | |
| 8,674,083 | B2 | 3/2014 | Presta | |
| 8,828,396 | B2 | 9/2014 | Heusser et al. | |
| 9,090,696 | B2 | 7/2015 | Barrett et al. | |
| 9,475,879 | B2 | 10/2016 | Suri et al. | |
| 10,435,475 | B2 | 10/2019 | Honczarenko et al. | |
| 11,220,550 | B2 | 1/2022 | Yamniuk et al. | |
| 11,254,750 | B2 | 2/2022 | Yamniuk et al. | |
| 11,261,258 | B2 | 3/2022 | Yamniuk et al. | |
| 11,613,585 | B2 | 3/2023 | Yamniuk et al. | |
| 11,773,178 | B2 | 10/2023 | Yamniuk et al. | |
| 11,795,231 | B2 | 10/2023 | Yamniuk et al. | |
| 11,926,673 | B2 | 3/2024 | Yamniuk et al. | |
| 12,419,953 | B2 * | 9/2025 | Yamniuk ............ | A61K 47/6849 |
| 2005/0054832 | A1 | 3/2005 | Lazar et al. | |
| 2006/0235208 | A1 | 10/2006 | Lazar et al. | |

(Continued)

FOREIGN PATENT DOCUMENTS

| | | |
|---|---|---|
| CN | 102633880 A | 8/2012 |
| CN | 102918063 A | 2/2013 |

(Continued)

OTHER PUBLICATIONS

Schwabe et al., 2018, Safety, pharmacokinetics and pharmacodynamics of multiple rising doses of BI 655064, an antagonistic anti-CD40 antibody in healthy subjects: a potential novel treatment for autoimmune diseases. *J Clin Pharmacol. 58*(12): 1566-1577.

(Continued)

*Primary Examiner* — Zachary C Howard
(74) *Attorney, Agent, or Firm* — Banner & Witcoff, Ltd.

(57) ABSTRACT

A method of treating an autoimmune disease such as Sjögren's Syndrome is provided. The method comprises administration of an antibody or an antigen binding portion thereof that specifically binds an epitope of CD40 associated with antagonism. The antibody or the antigen binding portion thereof does not exhibit CD40 agonist activity in either in vitro or in vivo preclinical testing. The antibody inhibits CD40L-induced signaling on DCs, resulting at least in part to reduced production of pro-inflammatory cytokines, and reduction of cell surface activation markers, CD86 and CD54. The antibodies can comprise an Fc region containing a mutation that reduces or eliminates binding to Fc receptors, reducing or eliminating Fc gamma receptor (FcγR)-mediated cross-linking or clustering.

17 Claims, 7 Drawing Sheets

Specification includes a Sequence Listing.

(56) References Cited

U.S. PATENT DOCUMENTS

| | | | |
|---|---|---|---|
| 2007/0003546 A1 | 1/2007 | Lazar et al. | |
| 2008/0051563 A1 | 2/2008 | Lazar et al. | |
| 2008/0057070 A1 | 3/2008 | Long et al. | |
| 2008/0199471 A1 | 8/2008 | Bernett et al. | |
| 2010/0104557 A1 | 4/2010 | Bernett et al. | |
| 2010/0331208 A1 | 12/2010 | Gao et al. | |
| 2011/0027276 A1 | 2/2011 | Bernett et al. | |
| 2013/0149238 A1 | 6/2013 | Kavlie et al. | |
| 2013/0209445 A1 | 8/2013 | Lazar et al. | |
| 2013/0236470 A1 | 9/2013 | Matsuoka et al. | |
| 2014/0079701 A1 | 3/2014 | Miller et al. | |
| 2014/0099317 A1 | 4/2014 | Suri et al. | |
| 2014/0294812 A1 | 10/2014 | Lazar | |
| 2014/0335089 A1 | 11/2014 | Igawa et al. | |
| 2014/0363428 A1 | 12/2014 | Igawa et al. | |
| 2015/0018529 A1 | 1/2015 | Humphreys et al. | |
| 2015/0210763 A1 | 7/2015 | Kuramochi et al. | |
| 2015/0299296 A1 | 10/2015 | Katada et al. | |
| 2015/0315284 A1 | 11/2015 | Lazar et al. | |
| 2015/0337053 A1 | 11/2015 | McCarthy et al. | |
| 2016/0039912 A1 | 2/2016 | Mimoto et al. | |
| 2016/0075785 A1 | 3/2016 | Ast et al. | |
| 2016/0145350 A1 | 5/2016 | Lonberg et al. | |
| 2016/0355596 A1 | 12/2016 | Honczarenko et al. | |
| 2016/0376371 A1 | 12/2016 | Ravetch et al. | |
| 2018/0289790 A1* | 10/2018 | Engelhardt | C07K 16/2818 |
| 2018/0340031 A1 | 11/2018 | Yamniuk et al. | |
| 2019/0153111 A1* | 5/2019 | Espie | A61P 37/02 |
| 2020/0148779 A1 | 5/2020 | Yamniuk et al. | |
| 2020/0157233 A1 | 5/2020 | Yamniuk et al. | |
| 2021/0054090 A1 | 2/2021 | Yamniuk et al. | |

FOREIGN PATENT DOCUMENTS

| | | | | |
|---|---|---|---|---|
| CN | 103172731 A | 6/2013 | | |
| CN | 103635488 A | 3/2014 | | |
| CN | 104788565 A | 7/2015 | | |
| CN | 104918957 A | 9/2015 | | |
| EP | 2471813 B1 | 12/2014 | | |
| JP | 2008-505174 A | 2/2008 | | |
| JP | 2010-514460 A | 5/2010 | | |
| JP | 2014-513953 A | 6/2014 | | |
| JP | 2014-530611 A | 11/2014 | | |
| JP | 2018-526977 A | 9/2018 | | |
| JP | 2020-518600 A | 6/2020 | | |
| JP | 2020-522494 A | 7/2020 | | |
| WO | WO-2000/042072 A2 | 7/2000 | | |
| WO | WO-2004/099249 A2 | 11/2004 | | |
| WO | WO-2005/044854 A2 | 5/2005 | | |
| WO | WO-2006/019447 A1 | 2/2006 | | |
| WO | WO-2006/127910 A2 | 11/2006 | | |
| WO | WO-2008/091954 A2 | 7/2008 | | |
| WO | WO-2008/137475 A2 | 11/2008 | | |
| WO | WO-2009-094391 A1 | 7/2009 | | |
| WO | WO-2011/123489 A2 | 10/2011 | | |
| WO | WO-2012/065950 A1 | 5/2012 | | |
| WO | WO-2012/145673 A1 | 10/2012 | | |
| WO | WO-2012/149356 A2 | 11/2012 | | |
| WO | WO-2013/056068 A1 | 4/2013 | | |
| WO | WO-2014/006217 A1 | 1/2014 | | |
| WO | WO-2014/070934 A1 | 5/2014 | | |
| WO | WO-2014/184545 A2 | 11/2014 | | |
| WO | WO-2015/0134988 A1 | 9/2015 | | |
| WO | WO-2016/028810 A1 | 2/2016 | | |
| WO | WO-2016/081746 A2 | 5/2016 | | |
| WO | WO-2016/081748 A2 | 5/2016 | | |
| WO | WO-2016/168716 A1 | 10/2016 | | |
| WO | WO-2016/196228 A1 | 12/2016 | | |
| WO | WO-2016/196314 A1 | 12/2016 | | |
| WO | WO-2017/004006 A1 | 1/2017 | | |
| WO | WO-2017/004016 A1 | 1/2017 | | |
| WO | WO-2017/059196 A2 | 4/2017 | | |
| WO | WO-2018/065389 A1 | 4/2018 | | |
| WO | WO-2018/169993 A1 | 9/2018 | | |
| WO | WO-2018/175279 A2 | 9/2018 | | |
| WO | WO-2018/204405 A1 | 11/2018 | | |
| WO | WO-2018/217976 A1 | 11/2018 | | |
| WO | WO-2018/218056 A1 | 11/2018 | | |
| WO | WO-2018/222722 A2 | 12/2018 | | |
| WO | WO-2018/231254 A1 | 12/2018 | | |
| WO | 2019087094 A1 | 5/2019 | | |
| WO | WO-2018/217988 A9 | 5/2019 | | |
| WO | WO-2020/102728 A1 | 5/2020 | | |
| WO | WO-2020106620 A1 | * | 5/2020 | C07K 16/2878 |
| WO | WO-2020/112781 A1 | 6/2020 | | |

OTHER PUBLICATIONS

Ralph et al., 2015, (THU0407) Preclinical characterization of a highly selective and potent antagonistic Anti-CD40 Mab. *Annals of the Rheumatic Diseases*, 74:344.

Slade et al., 2016, (FRI0230) Assessment of safety, pharmacokinetics and pharmacodynamics of a novel anti-CD40 monoclonal antibody, CFZ533, in healthy volunteers and in rheumatoid arthritis patients. *Annals of the Rheumatic Diseases*, 75:516-517.

"Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011).

Cai, B., et al, "C-terminal lysine processing of human immunoglobulin G2 heavy chain in vivo," Biotechnol Bioeng. Feb. 2011; 108(2):404-12, Abstract only.

Davies, Clare C., et al., "TRAF6 Is Required for TRAF2-Dependent CD40 Signal Transduction in Nonhemopoietic Cells," Molecular and Cellular Biology 2005, vol. 25, No. 22, pp. 9806-9819.

First Office Action issued Sep. 3, 2021 in Chinese Patent Application No. 201880032964.0 (9 pages) with an English translation (11 pages).

Hoogenboom, Hennie R., et al., "Multi-subunit proteins on the surface of filamentous phage: methodologies for displaying antibody (Fab) heavy and light chains," Nucleic Acids Research, vol. 19, No. 15, pp. 4133-4137.

International Preliminary Report on Patentability mailed Dec. 5, 2019 in International Application No. PCT/US2018/034315.

International Preliminary Report on Patentability mailed Dec. 5, 2019 in International Application No. PCT/US2018/034330.

International Preliminary Report on Patentability mailed Jun. 3, 2021 in International Application No. PCT/US2019/062011.

International Search Report and the Written Opinion mailed Apr. 9, 2020 in International Application No. PCT/US2019/062011.

International Search Report and Written Opinion mailed Jul. 24, 2018 for PCT/US2018/034330.

International Search Report mailed Sep. 11, 2018 in International Application No. PCT/US2018/034315.

Melvin et al., 2012, "Belatacept: A worthy alternative to cyclosporine?" J. Pharmacol Pharmacother. 3(1): 90-92.

Mimoto, F., et al., "Engineered antibody Fc variant with selectively enhanced Fc?RIIb binding over both Fc?RIIaR131 and Fc?RIIaH131," Protein Engineering, Design and Selection 2001, 26(10): 589-598.

Nebija et al., "2-DE and MALDI-TOF-MS analysis of therapeutic fusion protein abatacept," Electrophoresis 31: 1438-1443, 2011.

Ngo et al., "Computational Complexity, Protein Structure Prediction and the Levinthal Paradox," in: The Protein Folding Problem and Tertiary Structure Prediction (Boston, Birkhäuser, 1994), Chapter 14, pp. 434-495.

Ristov et al. (2018) "Characterization of the in vitro and in vivo properties of CFZ533, a blocking and non-depleting anti-CD40 monoclonal antibody," Am J Transplant. 18(12):2895-2904. [Epub May 2018 41.

Rowshanravan et al. 2018, "CTLA-4: a moving target in immunotherapy," Blood 131(1):58-97.

Shields et al., (2001) "High Resolution Mapping of the Binding Site on Human IgG1 for FcgRI, FcgRII, FcgRIII, and FcRn and Design of IgG1 Variants with Improved Binding to the FcgR*," The Journal of Biological Chemistry, vol. 276, No. 9, pp. 6591-6604.

(56) References Cited

OTHER PUBLICATIONS

Vidarsson, Gestur, et al., "IgG Subclasses and allotypes: from structure to effector functions," Frontiers in Immunology, vol. 5, Oct. 20, 2014, pp. 1-17.
Vonderheide, Robert H., et al., "Clinical Activity and Immune Modulation in Cancer Patients Treated with CP-870,893, a Novel CD40 Agonist Monoclonal Antibody," J Clin Oncol. 2007, 25(7): 876-883.
Wells, 1990, "Additivity of Mutational Effects in Proteins." Biochemistry 29(37): 8509-8517.
Written Opinion mailed Sep. 11, 2018 in International Application No. PCT/US2018/034315.
Adams, et al. (2005) "Development of a chimeric anti-CD40 monoclonal antibody that synergizes with LEA29Y to prolong islet allograft survival," J. Immunol. 174: 542-50.
Nov. 23, 2021—(WO) International Search Report and Written Opinion—App PCT/US2021/047610.
Fisher Benjamin A et al, "Assessment of the anti-CD40 antibody iscalimab in patients with primary Sjögren's syndrome: a multicentre, randomised, double-blind, placebo-controlled, proof-of-concept study", NL Mar. 3, 2020 (Mar. 3, 2020), vol. 2, No. 3, p. e142-e152, Retrieved from the Internet: URL:http://dx.doi.org/10.1016/S2665-9913(19)30135-3 XP055859370 DOI: 10.1016/S2665-9913(19)30135-3 external link ISSN:2665-9913.
Anonymous, "BMS-986325 in Healthy Participants and Participants With Primary Sjögren's Syndrome—Full Text View—ClinicalTrials.gov", Dec. 24, 2020 (Dec. 24, 2020), Retrieved from the Internet: URL:https://clinicaltrials.gov/ct2/show/NCT04684654 XP055859331 [retrieved on Nov. 9, 2021].
Anonymous, "Safety, Pharmacokinetics and Preliminary Efficacy Study of CFZ533 in Patients With Primary Sjögren's Syndrome—Full Text View—ClinicalTrials.gov", Nov. 14, 2014 (Nov. 14, 2014), Retrieved from the Internet: URL: https://clinicaltrials.gov/ct2/show/NCT02291029 XP055859384 [retrieved on Nov. 9, 2021].
Fisher Benjamin et al, "Abtract 1784: The Novel Anti-CD40 Monoclonal Antibody CFZ533 Shows Beneficial Effects in Patients with Primary Sjogren's Syndrome: A Phase IIa Double-Blind, PlaceboControlled Randomized Trial", Arthritis & Rheumatology, John Wiley & Sons, Inc, US, vol. 69, No. Suppl. 10, Sep. 18, 2017 (Sep. 18, 2017), XP002788011 ISSN:2326-5191.
Jobling Kerry et al, "CD40 as a therapeutic target in Sjögren's syndrome", GB Jul. 3, 2018 (Jul. 3, 2018), vol. 14, No. 7, p. 535-537, Retrieved from the Internet: URL:http://dx.doi.org/10.1080/1744666X.2018.1485492 XP055859366 DOI: 10.1080/1744666X.2018.1485492 external link ISSN:1744-666X.
Albach et al., 2018, Safety, pharmacokinetics and pharmacodynamics of single rising doses of BI 655064, an antagonistic anti-CD40 antibody in healthy subjects: a potential novel treatment for autoimmune diseases. *Eur J Clin Pharmacol*, 74: 161-169.
De Genst et al., 2006, "Antibody repertoire development in camelids," Dev Comp Immunol. 30(1-2):187-198.
Deschacht et al., 2010, "A novel promiscuous class of camelid single-domain antibody contributes to the antigen-binding repertoire," J Immunol. 184(10):5696-5704. Epub Apr. 19, 2010.
Tereshko et al., 2008. "Toward chaperone-assisted crystallography: protein engineering enhancement of crystal packing and X-ray phasing capabilities of a camelid single-domain antibody (VHH) scaffold," Protein Sci. 17(7):1175-1187.
Sircar et al., 2011, "Analysis and modeling of the variable region of camelid single-domain antibodies," J Immunol. 186(11):6357-6367.
Yu, X et al. (2018) "Complex Interplay between Epitope Specificity and Isotype Dictates the Biological Activity of Anti-human CD40 Antibodies" Cancer Cell 33(4): 664-675.e4.
Yamniuk AP et al. (2016) "Functional Antagonism of Human CD40 Achieved by Targeting a Unique Species-Specific Epitope" J Mol Biol. 428(14):2860-2879. Epub May 21, 2016.
Okimura K et al. (2014) "Characterization of ASKP1240, a fully human antibody targeting human CD40 with potent immunosuppressive effects" Am J Transplant. 4(6):1290-1299.
Laman JD et al. (2002) "Protection of marmoset monkeys against EAE by treatment with a murine antibody blocking CD40 (mu5D12)" Eur J Immunol. 32(8):2218-2128.
Cordoba et al., 2015, "A novel, blocking, Fc-silent anti-CD40 monoclonal antibody prolongs nonhuman primate renal allograft survival in the absence of B cell depletion," Am J Transplant. 15(11): 2825-36.
Luqman et al., 2008, "The antileukemia activity of a human anti-CD40 antagonist antibody, HCD122, on human chronic lymphocytic leukemia cells," Blood 112: 711-720.

* cited by examiner

FIGURE 1

BMS-986325 Heavy Chain Amino Acid Sequence:

QVQLVQSGAEVKKPGSSVKVSCKASGYAFTSYWMHWVRQAPGQGLEWMGQINPTTGRSQYN
EKFKTRVTITADKSTSTAYMELSSLRSEDTAVYYCARWGLQPFAYWGQGTLVTVSS*ASTKG*
*PSVFPLAPSSKSTSGGTAALGCLVKDYFPEPVTVSWNSGALTSGVHTFPAVLQSSGLYSLS*
*SVVTVPSSSLGTQTYICNVNHKPSNTKVDKRV*EPKSCDKTHTCPPCPAPELLGGKSVFLFP
PKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSRWQQGNVFSCSV
MHEALHNHYTQKSLSLSPG
(SEQ ID NO: 5)

BMS-986325 Light Chain Amino Acid Sequence:

DIQMTQSPSFLSASVGDRVTITCKASQDVSTAVAWYQQKPGKAPKLLIYSASYRYTGVPSR
FSGSGSGTDFTLTISSLQPEDFATYYCQQHYSTPWTFGGGTKVEIK*RTVAAPSVFIFPPSD*
*EQLKSGTASVVCLLNNFYPREAKVQWKVDNALQSGNSQESVTEQDSKDSTYSLSSTLTLSK*
*ADYEKHKVYACEVTHQGLSSPVTKSFNRGEC*
(SEQ ID NO: 11)

FIGURE 2A

| **Primary Pharmacodynamics** | | |
|---|---|---|
| Type of Study | Test System | Findings |
| CD40 binding affinity | Measurement of BMS-986325 binding to the extracellular domain of human, cynomolgus, rat, and mouse CD40 by SPR | BMS-986325 bound to human CD40 with a Kd of 5.3 nM and to cynomolgus CD40 with a Kd of 6.7 nM. Binding to mouse and rat CD40 was undetectable. |
| Binding to FcγRs | Measurement of BMS-986325 binding to the extracellular domain of CD32, CD16, and CD64 by SPR | Binding of BMS-986325 to CD16 and CD32 was undetectable. Binding of BMS-986325 was reduced 100× relative to wild type IgG1 containing proteins (Kd 17 nM). |
| Inhibition of B-cell proliferation | Soluble CD40L trimer stimulation of human tonsillar B cells | BMS-986325 inhibited B-cell proliferation with an IC50 of 0.04 ± 0.03 nM<br>(5.6 ± 3.9 ng/ml; n=10 donors). |
| | CD40L-expressing CHO cell stimulation of tonsillar B-cell proliferation | BMS-986325 inhibited B-cell proliferation with an IC50 of 0.28 + 0.07 nM<br>(39.9 ± 9.8 ng/ml; n=8 donors). |
| Whole blood human B-cell activation | Soluble CD40L trimer stimulation of human B cells in whole blood | BMS-986325 inhibits CD86 upregulation with an IC50 of 0.24 ± 0.06 nM<br>(34.2 ± 9.1 ng/ml; n=10 donors).<br>BMS-986325 inhibits CD54 upregulation with an IC50 of 0.24 ± 0.06 nM<br>(34.6 ± 8.7 ng/ml; n=10 donors). |
| Whole blood cynomolgus B-cell activation | Soluble CD40L trimer stimulation of cynomolgus B cells in whole blood | BMS-986325 inhibits CD86 upregulation with an IC50 of 0.25 ± 0.09 nM<br>(36.4 ± 12.4 ng/ml; n=8 donors). |
| Inhibition of cynomolgus B-cell proliferation | Stimulation of cynomolgus splenic B cells with soluble CD40L trimer or CD40L-expressing CHO cells | BMS-986325 inhibits splenic B-cell proliferation driven by CD40L-trimer with an IC50 of 0.19 ± 0.18 nM (27.8 ± 25.9 ng/ml; n=6 donors) and that driven by CD40L-expressing CHO cells with an IC50 of 4.5 ± 5.4 nM (650.5 ± 782.7 ng/ml; n=6 donors). |

FIGURE 2B

Primary Pharmacodynamics

| Type of Study | Test System | Findings |
|---|---|---|
| Inhibition of DC activation | Monocyte-derived DCs | BMS-986325 suppressed CHO CD40L-induced IL-6 production with an IC50 of 0.08 ± 0.04 nM (11.3 ± 5.3 μg/ml) and TNFα production with an IC50 of 0.1 ± 0.03 nM (13.3 ± 4.8 μg/ml); n=4 donors. |
| Binding of BMS-986325 to B cells | Direct binding of AF488-labeled BMS-986325 to B cells in human whole blood | AF488-labeled-BMS-986325 bound to CD20-positive B cells in human whole blood with a potency (EC50) of 0.90 ± 0.45 nM (130.4 ± 65.9 ng/ml; n=4 donors). |
| | Direct binding of AF488-labeled BMS-986325 to B cells in cynomolgus monkey whole blood | AF488-labeled-BMS-986325 bound to CD20-positive B cells in cynomolgus whole blood with a potency (EC50) of 1.0 nM (149.5 ng/ml; n=2 donors). |
| | Binding of BMS-986325 to B cells in cynomolgus whole blood using secondary anti-human IgG1-PE for detection | BMS-986325 bound to CD20-positive B cells in cynomolgus monkey whole blood with a potency (EC50) of 0.7 ± 0.15 nM (106.1 ± 22.6 ng/ml; n=4 donors). |
| Assay for agonism (B-cell proliferation or cytokine production) | BMS-986325 ability to stimulate tonsillar human B-cell proliferation or IL-6 production +/- IL-4 | BMS-986325 (at concentrations up to 10 μg/ml) did not increase B-cell proliferation or IL-6 production either alone or in combination of IL-4 with tonsillar B cells from 10 donors. |
| Assay for agonism (iDC activation or cytokine production) | Immature DCs incubated with BMS-986325 either alone or with the addition of FcγR-expressing cells (CHO-CD32) | BMS-986325, either alone or in the presence of CD32 expressing CHO cells, did not increase activation markers (CD86 or CD54 cell surface expression) or IL-6 production in immature DCs. Experiments were performed with cells from 10 different donors and concentrations up to 100 μg/ml of BMS-986325. |
| Activation of human B cells in whole blood | Assay for the ability of BMS-0986325 to increase CD54, CD69 or CD86 expression on B cells in human whole blood | BMS-986325 did not significantly increase CD54, CD69 or CD86 expression on B cells in whole blood from 6 donors at concentrations up to 12 μg/ml. |

FIGURE 2C

| Primary Pharmacodynamics | | |
|---|---|---|
| Type of Study | Test System | Findings |
| Activation of CD40-NFκB reporter assay | Sensitive CD40-NFkB reporter assay in RAMOS B cell line +/- co-expression with FcγR (CD32) | BMS-986325 did not activate CD40-NFκB reporter at concentrations up to 10 µg/ml (n=3 independent experiments) either with or without CD32 co-expression. |
| Lack of effector function with BMS-986325 | ADDC, CDC, and ADCP | BMS-986325 did not induce ADCC-, CDC- or ADCP-mediated killing of CD40-expressing target cells.<br>BMS 986325 did not induce ADCC-mediated lysis by NK effector cells on Raji cells expressing CD40, whereas positive control rituximab did.<br>BMS-986325 did not induce CDC, whereas positive control rituximab did.<br>BMS-986325 did not induce phagocytosis of CD40-expressing Raji cells. |

FIGURE 3

| Type of Study/ Species/ Strain | Schedule/ Route/ Duration of Study/ Vehicle/ Formulation | Range of Doses (mg/kg) | Animals per group (M/F) | Noteworthy Findings |
|---|---|---|---|---|
| **Primary Pharmacodynamics** | | | | |
| In vivo RO, target engagement and PD responses | RO and inhibition of soluble CD40L trimer stimulation of B-cell activation and T cell-dependent antibody responses to KLH immunization | 1, 10, and 100 mg/kg SC | 2M/2F | There was a dose-dependent duration of B-cell RO and PD responses in dosed animals. Complete RO was observed at all doses through Day 8, with RO falling to baseline by Day 18 for 1 mg/kg, and by Day 43 for 10 mg/kg. Full RO was maintained for the entire 43 days of the study at 100 mg/kg. On average, complete inhibition of a PD response (CD40L-induced B-cell activation) was observed through Day 8 at all doses. Recovery of the PD response was dose-dependent, observed by Day 15 at 1 mg/kg, Day 43 at 10 mg/kg, and maintenance of the PD response through Day 43 at 100 mg/kg. Additionally, suppression of the antibody response to an immunization with KLH was observed when ROs were maintained at ~ > 90%, through Day 29 at doses ≥ 10 mg/kg. |

FIGURE 4

| Projected Safety and Efficacy Margins of BMS-986325 for SAD Intravenous Doses (Part A1-A9) | | | | | | |
|---|---|---|---|---|---|---|
| Cohort Process | Dose[a] (mg) | Predicted Exposure | | NOAEL[b] Approach | | MABEL Approach |
| | | Cmax[a] (µg/mL) | AUC(INF)[a] (µg/mL·h) | Cmax Margin | AUC Margin | Max CD40 RO[a,c] (%) |
| A1 | 0.3 | 0.09 | 0.57 | 26,111 | 1,192,982 | 39.5 |
| A2 | 1 | 0.3 | 2.4 | 7,833 | 283,333 | 35.9 |
| A3 | 3 | 1 | 12 | 2,350 | 56,667 | 64.7 |
| A4 | 10 | 4 | 79 | 588 | 8,608 | 86.6 |
| A5 | 30 | 11 | 436 | 214 | 1560 | 95.2 |
| A6 | 100 | 37 | 2,495 | 64 | 273 | 98.5 |
| A7 | 300 | 111 | 11,219 | 21 | 61 | 99.5 |
| A8 | 600 | 223 | 27,061 | 11 | 25 | 99.8 |
| A9 | 1000 | 371 | 49,871 | 6 | 14 | 99.8 |

a: Based on an infusion duration of 60 minutes.

b: NOAEL is 100 mg/kg IV from 1-month GLP toxicology-monkey study (Cmax = 2,350 µg/mL and AUC = 680,000 µg/mL • h).

c: Based on maximum dose for a 70-kg human.

FIGURE 5

Projected Safety Margins for BMS-986325

| Species/Study | NOAEL Dose mg/kg | Cmax µg/mL | AUC (0-168 h) µg•h/mL | Total AUC (4 weeks)[a] µg•h/mL | Nonclinical Margins at FIH SAD Doses[b] | | | |
|---|---|---|---|---|---|---|---|---|
| | | | | | Parameter | IV | | SC |
| | | | | | | 0.3 mg | 1000 mg | 300 mg |
| Cynomolgus Monkey / 1-Month (qw) | 100 | 2,350 | 170,000 | 680,000 | **Dose (mg/kg):** | 23,333 | 7 | 23 |
| | | | | | **AUC:** | 1,192,982 | 14 | 80 |
| | | | | | **Cmax:** | 26,111 | 6 | 55 |

| Phase 1 Clinical Trial Human Dose Projection | Dose mg | Predicted Cmax µg/mL | Predicted AUC(INF) µg•h/mL |
|---|---|---|---|
| SAD starting dose | 0.3 | 0.09 | 0.57 |
| SAD maximum IV dose | 1000 | 371 | 49,871 |
| SAD SC dose | 300 | 43 | 8,567 |

a: The AUC(0-168h) after the last weekly dose in monkeys was multiplied by 4 to normalize for the total dosing interval of 4 weeks of exposure (Total AUC[4 weeks]) in the 1-month toxicity study.

b: Based on maximum dose for a 70-kg human.

METHOD OF TREATING AN AUTOIMMUNE DISEASE WITH ANTAGONISTIC CD40 MONOCLONAL ANTIBODIES

CROSS REFERENCE TO RELATED APPLICATIONS

This application is a national stage application (under 35 U.S.C. § 371) of PCT/US2021/047610, filed on Aug. 25, 2021, which claims the benefit of U.S. Provisional Application No. 63/070,209, filed Aug. 25, 2020, each of which is hereby incorporated in its entirety for all purposes.

SEQUENCE LISTING

The instant application contains a Sequence Listing that has been submitted electronically in ASCII format and is hereby incorporated by reference in its entirety. Said ASCII copy, created on Feb. 12, 2023, is named 009616_00242_US_SL.txt and is 53,515 bytes in size.

FIELD

The disclosure provides methods of treating an autoimmune disease with antibodies that bind CD40 and do not exhibit CD40 agonist activity. The antibodies comprise a modified IgG1 Fc domain, and exhibit minimal activation of immature dendritic cells. Appropriate doses and administration regimens for the anti-CD40 antibodies are also provided.

BACKGROUND

CD40 is a co-stimulatory molecule belonging to the tumor necrosis factor (TNF) receptor superfamily that is present on antigen presenting cells (APC), including dendritic cells, B cells, and macrophages. APCs are activated when CD40 binds its ligand, CD154 (CD40L), on TH cells. CD40-mediated APC activation is involved in a variety of immune responses, including cytokine production, up-regulation of co-stimulatory molecules (such as CD86), and enhanced antigen presentation and B cell proliferation. CD40 can also be expressed by endothelial cells, smooth muscle cells, fibroblasts, and epithelial cells.

CD40 activation is also involved in a variety of undesired T cell responses related to autoimmunity, transplant rejection, or allergic responses, for example. One strategy for controlling undesirable T cell responses is to target CD40 with an antagonistic antibody. For example, monoclonal antibody HCD122 (Lucatumumab), formerly known as Chiron 1212, is currently in clinical trials for the treatment of certain CD40-mediated inflammatory diseases. See "Study of HCD122 (Lucatumumab) and Bendamustine Combination Therapy in $CD40^+$ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011). Monoclonal antibodies, however, can display agonist activity. For example, the usefulness of the anti-CD40 antibody, Chi220, is limited by its weak stimulatory potential. See Adams, et al., "Development of a chimeric anti-CD40 monoclonal antibody that synergizes with LEA29Y to prolong islet allograft survival," J. Immunol. 174: 542-50 (2005).

SUMMARY

Provided is a method of treating an autoimmune disease in a human patient in need of such treatment, comprising administering to the patient a therapeutically effective amount of the antibody polypeptide disclosed herein. In an embodiment, the autoimmune disease is Sjögren's Syndrome.

The method comprises administering a monoclonal antibody directed against an epitope of CD40 associated with antagonism. In an embodiment, the monoclonal antibody is BMS-986325. The disclosed antibodies potently inhibits CD40 signaling in B-cell proliferation driven both by soluble CD40L and cell-associated CD40L. Additionally, disclosed antibodies inhibit CD40L-induced signaling on DCs, resulting in reduced production of pro-inflammatory cytokines, and reduction of cell surface activation markers, CD86 and CD54. The disclosed antibodies are fully cross-reactive with CD40 from cynomolgus monkey, and treatment of cynomolgus monkeys with disclosed antibodies leads to dose-dependent receptor engagement, reduction of CD40L-driven B-cell activation ex vivo and suppression of a T-cell-dependent antibody response (TDAR). Further, disclosed antibodies comprise a fragment crystallizable (Fc) region containing a mutation that reduces or eliminates binding to Fc receptors, eliminating Fc gamma receptor (FcγR)-mediated cross-linking or clustering. Importantly, disclosed antibodies exhibit no evidence of CD40 agonism in either in vitro or in vivo preclinical testing.

The method is practiced by administering to the patient at least one dose of an isolated antibody, or antigen binding portion thereof, that specifically binds to human CD40, wherein the antibody comprises a first polypeptide portion comprising a heavy chain variable region, and a second polypeptide portion comprising a light chain variable region, wherein:

- the heavy chain variable region comprises (i) a CDR1 comprising SYWMH (SEQ ID NO: 1), a CDR2 comprising QINPTTGRSQYNEKFKT (SEQ ID NO: 2), and a CDR3 comprising WGLQPFAY (SEQ ID NO: 3); and
- the light chain variable region comprises a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9),
- wherein the dose is selected from 0.3 milligram (mg) to 1000 mg of the antibody, or antigen binding portion thereof.

In an embodiment, the method is practiced an isolated antibody or antigen binding portion thereof, wherein the antibody comprises a first polypeptide portion comprising a heavy chain variable region, and a second polypeptide portion comprising a light chain variable region, wherein:

the heavy chain variable region comprises the amino acid sequence of (SEQ ID NO: 4)

QVQLVQSGAEVKKPGSSVKVSCKASGYAFTSYWMHWVRQAPGQGLEWMG QINPTTGRSQYNEKFKTRVTITADKSTSTAYMELSSLRSEDTAVYYCAR WGLQPFAYWGQGTLVTVSS, and the light chain variable region comprises the amino acid sequence of (SEQ ID NO: 10)

DIQMTQSPSFLSASVGDRVTITCKASQDVSTAVAWYQQKPGKAPKLLIY SASYRYTGVPSRFSGSGSGTDFTLTISSLQPEDFATYYCQQHYSTPWTF GGGTKVEIK.

In certain embodiments of the method, the isolated antibody or antigen binding portion thereof comprises the first polypeptide portion comprising a human heavy chain constant region; and the second polypeptide portion comprising a human light chain constant region. The isolated antibody or antigen binding portion thereof described herein comprises a human IgG1 Fc domain comprising a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion thereof has reduced FcγR binding. In an embodiment, the proline at Kabat position 238 is substituted with lysine.

The isolated antibody or antigen binding portion thereof described herein can comprise an Fc domain which comprises an amino acid sequence selected from:

(SEQ ID NO: 13; IgG1-P238K (-C-term Lys))
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG, (SEQ ID NO: 14; IgG1-P238K)
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK, (SEQ ID NO: 15; CH1-IgG1-P238K (-C-term Lys))
*ASTKGPSVFPLAPSSKSTSGGTAALGCLVKDYFPEPVTVSWNSGALTSG*
*VHTFPAVLQSSGLYSLSSVVTVPSSSLGTQTYICNVNHKPSNTKVDKRV*
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG, (SEQ ID NO: 16; CH1-IgG1-P238K)
*ASTKGPSVFPLAPSSKSTSGGTAALGCLVKDYFPEPVTVSWNSGALTSG*
*VHTFPAVLQSSGLYSLSSVVTVPSSSLGTQTYICNVNHKPSNTKVDKRV*
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ -continued VSLTCLVKGFYPSDIAVEWESNGQPENNYKTTPPVLDSDGSFFLYSKLT
VDKSRWQQGNVFSCSVMHEALHNHYTQKSLSLSPGK, (SEQ ID NO: 17; IgG1f-P238K (-C-term Lys))
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPG, (SEQ ID NO: 18; IgG1f-P238K)
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPGK, (SEQ ID NO: 19; CH1-IgG1f-P238K (-C-term Lys))
*ASTKGPSVFPLAPSSKSTSGGTAALGCLVKDYFPEPVTVSWNSGALTSG*
*VHTFPAVLQSSGLYSLSSVVTVPSSSLGTQTYICNVNHKPSNTKVDKRV*
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPG,
or (SEQ ID No: 20; CH1-IgG1f-P238K)
*ASTKGPSVFPLAPSSKSTSGGTAALGCLVKDYFPEPVTVSWNSGALTSG*
*VHTFPAVLQSSGLYSLSSVVTVPSSSLGTQTYICNVNHKPSNTKVDKRV*
EPKSCDKTHTCPPCPAPELLGGKSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPGK.

The isolated antibody or antigen binding portion thereof can comprise a human IgG1 Fc domain comprising the amino acid sequence of SEQ ID NO: 13 or SEQ ID NO: 14.

In some embodiments, the method is practiced with an isolated antibody or antigen binding portion thereof described herein, wherein the first polypeptide portion comprises or consists of an amino acid sequence selected from the group consisting of:

(SEQ ID NO: 5; HC_Y12XX-hz28-CH1-IgG1-P238K-no terminal lysine)
QVQLVQSGAEVKKPGSSVKVSCKASGYAFTSYWMHWVRQAPGQG
LEWMGQINPTTGRSQYNEKFKTRVTITADKSTSTAYMELSSLRSEDTAV
YYCARWGLQPFAYWGQGTLVTVSS*ASTKGPSVFPLAPSSKSTSGGTAAL*
*GCLVKDYFPEPVTVSWNSGALTSGVHTFPAVLQSSGLYSLSSVVTVPSS*
*SLGTQTYICNVNHKPSNTKVDKRV*EPKSCDKTHTCPPCPAPELLGGKSV
FLFPPKPKDTLMISRTPEVTCVVVDVSHEDPEVKFNWYVDGVEVHNAKT -continued

KPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHY

TQKSLSLSPG, (SEQ ID NO: 6; HC_Y12XX-hz28-CH1-IgG1-P238K-with terminal lysine)
QVQLVQSGAEVKKPGSSVKVSCKASGYAFTSYWMHWVRQAPGQG

LEWMGQINPTTGRSQYNEKFKTRVTITADKSTSTAYMELSSLRSEDTAVYYCAR

WGLQPFAYWGQGTLVTVSS*ASTKGPSVFPLAPSSKSTSGGTAALGCLVKDYFPEPVTV*

*SWNSGALTSGVHTFPAVLQSSGLYSLSSVVTVPSSSLGTQTYICNVNHKPSNTKVDKRV*EP

KSCDKTHTCPPCPAPELLGGKSVFLFPPKPKDTLMISRTPEVTCVVVDVSHEDPEVK

FNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQK

SLSLSPGK, (SEQ ID NO: 21; HC_Y12XX-hz28-CH1-IgG1f-P238K-no terminal lysine)
QVQLVQSGAEVKKPGSSVKVSCKASGYAFTSYWMHWVRQAPGQG

LEWMGQINPTTGRSQYNEKFKTRVTITADKSTSTAYMELSSLRSEDTAVYYCAR

WGLQPFAYWGQGTLVTVSS*ASTKGPSVFPLAPSSKSTSGGTAALGCLVKDYFPEPVTV*

*SWNSGALTSGVHTFPAVLQSSGLYSLSSVVTVPSSSLGTQTYICNVNHKPSNTKVDKRV*EP

KSCDKTHTCPPCPAPELLGGKSVFLFPPKPKDTLMISRTPEVTCVVVDVSHEDPEVK

FNWYVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQK

SLSLSPG,
and (SEQ ID NO: 22; HC_Y12XX-hz28-CH1-IgG1f-P238K-with terminal lysine)
QVQLVQSGAEVKKPGSSVKVSCKASGYAFTSYWMHWVRQAPGQG

LEWMGQINPTTGRSQYNEKFKTRVTITADKSTSTAYMELSSLRSEDTAVYYCAR

WGLQPFAYWGQGTLVTVSS*ASTKGPSVFPLAPSSKSTSGGTAALGCLVKDYFPEPVTV*

*SWNSGALTSGVHTFPAVLQSSGLYSLSSVVTVPSSSLGTQTYICNVNHKPSNTKVDKRV*EP

KSCDKTHTCPPCPAPELLGGKSVFLFPPKPKDTLMISRTPEVTCVVVDVSHEDPEVK

FNWYVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQK

SLSLSPGK;

and the second polypeptide portion comprises or consists of the amino acid sequence of (SEQ ID NO: 11; LC_Y12XX-hz28-CL)
DIQMTQSPSFLSASVGDRVTITCKASQDVSTAVAWYQQKPGKAPKL

LIYSASYRYTGVPSRFSGSGSGTDFTLTISSLQPEDFATYYCQQHYSTP

WTFGGGTKVEIK*RTVAAPSVFIFPPSDEQLKSGTASVVCLLNNFYPREA*

-continued

*KVQWKVDNALQSGNSQESVTEQDSKDSTYSLSSTLTLSKADYEKHKVYA*

*CEVTHQGLSSPVTKSFNRGEC.*

In some embodiments, the method is practiced with the antibody or antigen binding portion thereof as described herein, wherein the first polypeptide portion comprises or consists of an amino acid sequence of (SEQ ID NO: 5; HC_Y12XX-hz28-CH1-IgG1-P238K-no terminal lysine)
QVQLVQSGAEVKKPGSSVKVSCKASGYAFTSYWMHWVRQAPGQGLEWM GqINPTTGRSQYNEKFKTRVTITADKSTSTAYMELSSLRSEDTAVYYCARWGLQP

FAYWGQGTLVTVSS*ASTKGPSVFPLAPSSKSTSGGTAALGCLVKDYFPEPVTVSWNSGA*

*LTSGVHTFPAVLQSSGLYSLSSVVTVPSSSLGTQTYICNVNHKPSNTKVDKRV*EPKSCDKT

HTCPPCPAPELLGGKSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG;

and the second polypeptide portion comprises or consists of the amino acid sequence of (SEQ ID NO: 11; LC_Y12XX-hz28-CL)
DIQMTQSPSFLSASVGDRVTITCKASQDVSTAVAWYQQKPGKAPKLLIYSASYRYT

GVPSRFSGSGSGTDFTLTISSLQPEDFATYYCQQHYSTPWTFGGGTKVEIK*RTVAAP*

*SVFIFPPSDEQLKSGTASVVCLLNNFYPREAKVQWKVDNALQSGNSQESVTEQDSKDSTY*

*SLSSTLTLSKADYEKHKVYACEVTHQGLSSPVTKSFNRGEC*.

In some embodiments, the method is practiced with the antibody BMS-986325 wherein the first polypeptide portion has the amino acid sequence of (SEQ ID NO: 5; HC_Y12XX-hz28-CH1-IgG1-P238K-no terminal lysine)
QVQLVQSGAEVKKPGSSVKVSCKASGYAFTSYWMHWVRQAPGQGLEWM GqINPTTGRSQYNEKFKTRVTITADKSTSTAYMELSSLRSEDTAVYYCARWGLQP

FAYWGQGTLVTVSS*ASTKGPSVFPLAPSSKSTSGGTAALGCLVKDYFPEPVTVSWNSGA*

*LTSGVHTFPAVLQSSGLYSLSSVVTVPSSSLGTQTYICNVNHKPSNTKVDKRV*EPKSCDKT

HTCPPCPAPELLGGKSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPG;

and the second polypeptide portion has the amino acid sequence of (SEQ ID NO: 11; LC_Y12XX-hz28-CL)
DIQMTQSPSFLSASVGDRVTITCKASQDVSTAVAWYQQKPGKAPKLLIY

SASYRYTGVPSRFSGSGSGTDFTLTISSLQPEDFATYYCQQHYSTPWTF

GGGTKVEIK*RTVAAPSVFIFPPSDEQLKSGTASVVCLLNNFYPREAKVQ*

*WKVDNALQSGNSQESVTEQDSKDSTYSLSSTLTLSKADYEKHKVYACEV*

*THQGLSSPVTKSFNRGEC*.

In the methods disclosed, the isolated antibody or antigen binding portion thereof described herein can be a chimeric antibody. The isolated antibody or antigen binding portion thereof described herein can be a humanized antibody. The isolated antibody or antigen binding portion thereof described herein can comprise a human heavy chain constant region and a human light chain constant region.

In the methods disclosed, the antibody or antigen binding portion thereof disclosed herein, is an antigen binding portion selected from the group consisting of Fv, Fab, F(ab')2, Fab', dsFv, scFv, sc(Fv)2, diabodies, and scFv-Fc. The isolated antibody or antigen binding portion thereof as described herein can be an scFv-Fc.

The antibody or antigen binding portion thereof disclosed herein can linked to a therapeutic agent.

The antibody or antigen binding portion thereof disclosed herein can be linked to a second functional moiety having a different binding specificity than said antibody or antigen binding portion thereof.

The antibody or antigen binding portion thereof disclosed herein can further comprise an additional moiety.

Optionally, the antibody, or the antigen-binding portion thereof, is administered with an immunosuppressive/immunomodulatory and/or anti-inflammatory agent. Administration may be simultaneous or sequential. An exemplary agent is a CTLA4 mutant molecule, such as L104EA29Y-Ig (belatacept). In such a method of treating or preventing an autoimmune or inflammatory disease in a subject, the subject preferably has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), lupus nephritis, lupus nephritis, systemic lupus erythematosus, multiple sclerosis, myasthenia gravis, pemphigus, psoriasis, rheumatic fever, rheumatoid arthritis, sarcoidosis, scleroderma, Sjögren's syndrome, spondyloarthropathies, thyroiditis, transplant rejection, vasculitis, and ulcerative colitis.

Also contemplated is an antibody, or antigen binding portion thereof as disclosed herein, for use as a medicament for an autoimmune disease, such as Sjögren's syndrome. Further contemplated is an antibody, or antigen binding portion thereof as disclosed here, or a medicament comprising the same, for use to treat a subject in need thereof, for instance a subject diagnosed with Sjögren's syndrome. Further contemplated is an antibody, or antigen binding portion thereof as disclosed herein in a therapeutically-effective amount, for use in treating or preventing an autoimmune disease such as Sjögren's syndrome, wherein the antibody or antigen binding portion thereof is for administering to a patient in need thereof.

BRIEF DESCRIPTION OF THE FIGURES

FIG. 1 depicts the amino acid sequences of the heavy chain and the light chain of BMS-986325.

FIGS. 2A-2C depicts a summary of in vitro primary pharmacodynamics data for BMS-986325. Abbreviations: ADCC, antibody-dependent cellular cytotoxicity; ADCP, antibody-dependent cellular phagocytosis; CD40L, CD40 ligand; CDC, complement dependent cytotoxicity; CHO, Chinese hamster ovary; DCs, dendritic cells; EC50, concentration required for 50% maximal effect; FcγR, Fc gamma receptor; IC50, concentration at which 50% inhibition observed; iDC, monocyte-derived dendritic cells; IgG1, immunoglobulin G1; IL, interleukin; Kd, dissociation constant; NA, not available; NK, natural killer cells; SPR, surface plasmon resonance.

FIG. 3 depicts a summary of in vivo primary pharmacodynamics data for BMS-986325 Abbreviations: CD40L, CD40 ligand; F, female; KLH, keyhole limpet hemocyanin; M, male; NA, not available; PD, pharmacodynamics; RO, receptor occupancy; SC, subcutaneous.

FIG. 4 depicts a SAD dose escalation scheme and the corresponding projected safety and efficacy margins of BMS-986325 for SAD intravenous doses. Abbreviations: AUC(INF), area under the concentration-time curve from time zero to infinity; Cmax, maximum observed concentration; IV, intravenous; MABEL, minimum anticipated biological effect level; NOAEL, no-observed-adverse-effect level; RO, receptor occupancy; RO, receptor occupancy; SAD, single-ascending dose.

FIG. 5 depicts safety margins for BMS-986325 calculated from a 1-month GLP-toxicology study in monkeys. Abbreviations: AUC, area under the concentration-time curve; Cmax, maximum observed concentration; FIH, first-in-human; GLP Good Laboratory Practice; INF, infinity; IV, intravenous; NOAEL, no observed adverse effect (dose) level; SAD, single-ascending dose; SC, subcutaneous; qw, once weekly.

DETAILED DESCRIPTION

The present disclosure is directed to a method of treating an autoimmune disease such as Sjögren's Syndrome in a human patient by administration of antagonistic anti-CD40 antibodies. For therapeutic targets such as CD40, FcγR-mediated cross-linking of anti-CD40 antibodies has the potential to lead to undesirable agonist signaling and potential for toxicity. The methods of the present disclosure administer an antagonistic anti-CD40 antibody having reduced engagement of the "low affinity" FcγRs: hCD32a/FcγRIIa, hCD32b/FcγRIIb, and hCD16a/FcγRIIIa, as well as reduced engagement to "high affinity" FcγR hCD64. Reduced engagement of low affinity FcγRs is expected to reduce the likelihood of undesirable agonist signaling and undesirable potential for toxicity.

Definitions & Abbreviations

Further abbreviations and definitions are provided below.

APC antigen presenting cells

CD54 also referred to as ICAM-1

CDR complementarity determining regions $C_H$ or CH constant heavy chain $C_L$ or CL constant light chain CHO cell Chinese hamster ovary cell dAb domain antibody DC dendritic cell DTPA diethylenetriaminepentaacetic acid FcgR interchangeable with FcγR FcγR Fc-g amma-receptor FR Framework region GM-CSF granulocyte macrophage colony stimulating factor HC heavy chain ICAM-1 intracellular adhesion molecule 1 iDC immature dendritic cells

IFN interferon

IgG immunoglobulin G

IL-6 interleukin-6

LC light chain mAb monoclonal antibody mg milligram ml or mL milliliter ng nanogram nM nanomolar Pentetic acid diethylenetriaminepentaacetic acid PD pharmacodynamics pI isoelectric point PK pharmacokinetics q2wk once every two weeks qwk once a week SPR surface plasmon resonance TDAR T-cell-dependent antibody response TNF tumor necrosis factor μg microgram μM micromolar $V_L$ or VL variable light chain domain Vk or VK kappa variable light chain domain $V_H$ or VH variable heavy chain domain In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

As used here, the term "about" is understood by persons of ordinary skill in the art and will vary to some extent on the context in which it is used. Generally, "about" encompasses a range of values that are plus/minus 10% of a referenced value unless indicated otherwise in the specification.

It is understood that any and all whole or partial integers between the ranges set forth are included herein.

CD40 is also known and referred to as B-cell surface antigen CD40, Bp50, CD40L receptor, CDw40, CDW40, MGC9013, p50, TNFRSF5, and Tumor necrosis factor receptor superfamily member 5. "Human CD40" refers to the CD40 comprising the following amino acid sequence:

(SEQ ID NO: 12)

MVRLPLQCVL WGCLLTAVHP EPPTACREKQ YLINSQCCSL

CQPGQKLVSD CTEFTETECL PCGESEFLDT WNRETHCHQH

KYCDPNLGLR VQQKGTSETD TICTCEEGWH CTSEACESCV

LHRSCSPGFG VKQIATGVSD TICEPCPVGF FSNVSSAFEK

CHPWTSCETK DLVVQQAGTN KTDVVCGPQD RLRALVVIPI

IFGILFAILL VLVFIKKVAK KPTNKAPHPK QEPQEINFPD

DLPGSNTAAP VQETLHGCQP VTQEDGKESR ISVQERQ.

As used herein, the term "variable domain" refers to immunoglobulin variable domains defined by Kabat et al., Sequences of Immunological Interest, 5th ed., U.S. Dept. Health & Human Services, Washington, D.C. (1991). The numbering and positioning of CDR amino acid residues within the variable domains is in accordance with the well-known Kabat numbering convention. VH, "variable heavy chain" and "variable heavy chain domain" refer to the variable domain of a heavy chain. VL, "variable light chain" and "variable light chain domain" refer to the variable domain of a light chain.

The term "human," when applied to antibodies, means that the antibody has a sequence, e.g., FR and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above.

An "isolated" compound as used herein means that the compound is removed from at least one component with which the compound is naturally associated with in nature.

The anti-CD40 antibody of the present disclosure comprise a variable heavy chain and a variable light chain, each of which contains three complementarity-determining regions (CDRs) and four framework regions (FRs), arranged from amino-terminus to carboxy-terminus in the following order: FR1, CDR1, FR2, CDR2, FR3, CDR3, FR4. The CDRs contain most of the residues that form specific interactions with the antigen and are primarily responsible for antigen recognition.

The methods of the present disclosure administer an anti-CD40 antibody comprising CDRs of humanized antibody Y12XX-hz28 (Vh-hz14; Vk-hz2) and a human IgG1 Fc domain comprising a mutation at Kabat position 238 that reduces binding to Fc-gamma-receptors (FcγRs). See US Publication No. 2020-0157233. An overview of the amino acid sequences of the heavy chain variable region and light chain variable region is provided in Table 1. The table includes a short hand name and a more detailed name for each amino acid sequence, as well as the sequence identifiers.

TABLE 1

| Antibody | HC Variable Region | LC Variable Region |
|---|---|---|
| Y12XX-hz28 | Vh-hz14<br>QVQLVQSGAEVKKPGSSVKVSCKASGYAFTSYWMHWVRQAPGQGLEWMGQINPTTGRSQYNEKFKTRVTITADKSTSTAYMELSSLRSEDTAVYYCARWGLQPFAYWGQGTLVTVSS (SEQ ID NO: 4) | Vk-hz2<br>DIQMTQSPSFLSASVGDRVTITCKASQDVSTAVAWYQQKPGKAPKLLIYSASYRYTGVPSRFSGSGSGTDFTLTISSLQPEDFATYYCQQHYSTPWTFGGGTKVEIK (SEQ ID NO: 10) |

In a specific embodiment, the anti-CD40 antibodies of the present disclosure comprises the CDRs of humanized antibody YT2XX-hz28 (Vh-hz14; Vk-hz2). Details of the amino acid sequences of YT2XX-hz28 are provided in Table 2.

TABLE 2

| Y12XX-hz28 sequences (Vh-hz14; Vk-hz2) | | |
|---|---|---|
| Heavy chain variable region | QVQLVQSGAEVKKPGSSVKVSCKASGYAFT**SYWMH**WVRQAPGQGLEWMG**QINPTTGRSQYNEKFKT**RVTITADKSTSTAYMELSSLRSEDTAVYYCAR**WGLQPFAY**WGQGTLVTVSS SEQ ID NO: 4) | Vh-hz14 (SEQ ID NO: 4; CDRs underlined) |
| VH-CDR1 | SYWMH SEQ ID NO: 1) | Amino acids 31-35 of SEQ ID NO: 4 |
| VH-CDR2 | QINPTTGRSQYNEKFKT (SEQ ID NO: 2) | Amino acids 50-66 of SEQ ID NO: 4 |
| VH-CDR3 | WGLQPFAY (SEQ ID NO: 3) | Amino acids 99-106 of SEQ ID NO: 4 |
| HC_Y12XX-hz28-CH1-IgG1-P238K (is IgG1 with and without C-terminal lysine) | QVQLVQSGAEVKKPGSSVKVSCKASGYAFT**SYWMH**WVRQAPGQGLEWMG**QINPTTGRSQYNEKFKT**RVTITADKSTSTAYMELSSLRSEDTAVYYCAR**WGLQPFAY**WGQGTLVTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV*EPKSCDKTHTCPPCPAPELLGGKSVFLFPPKPKDTLMISRTPEVTCVVVDVSHEDPEVKFNWYV | CDRs underlined; CH1 = amino acids 118-215 (italicized); IgG1-P238K = amino acids 216-446; P238K underlined; no C-terminal lysine |

TABLE 2-continued

| Y12XX-hz28 sequences (Vh-hz14; Vk-hz2) | | |
|---|---|---|
| | DGVEVHNAKTKPREEQYNSTYRVVSVLTVLH<br>QDWLNGKEYKCKVSNKALPAPIEKTISKAKG<br>QPREPQVYTLPPSRDELTKNQVSLTCLVKGF<br>YPSDIAVEWESNGQPENNYKTTPPVLDSDGS<br>FFLYSKLTVDKSRWQQGNVFSCSVMHEALHN<br>HYTQKSLSLSPG<br>(SEQ ID NO: 5) | |
| | QVQLVQSGAEVKKPGSSVKVSCKASGYAFT**S**<br>**YWMH**WVRQAPGQGLEWMG**QINPTTGRSQYNE**<br>**KFKT**RVTITADKSTSTAYMELSSLRSEDTAV<br>YYCAR**WGLQPFAY**WGQGTLVTVSS*ASTKGPS*<br>*VFPLAPSSKSTSGGTAALGCLVKDYFPEPVT*<br>*VSWNSGALTSGVHTFPAVLQSSGLYSLSSVV*<br>*TVPSSSLGTQTYICNVNHKPSNTKVDKRV*EP<br>KSCDKTHTCPPCPAPELLGGKSVFLFPPKPK<br>DTLMISRTPEVTCVVVDVSHEDPEVKFNWYV<br>DGVEVHNAKTKPREEQYNSTYRVVSVLTVLH<br>QDWLNGKEYKCKVSNKALPAPIEKTISKAKG<br>QPREPQVYTLPPSRDELTKNQVSLTCLVKGF<br>YPSDIAVEWESNGQPENNYKTTPPVLDSDGS<br>FFLYSKLTVDKSRWQQGNVFSCSVMHEALHN<br>HYTQKSLSLSPGK<br>(SEQ ID NO: 6) | CDRs underlined; CH1 = amino acids 118-215 (italicized); IgG1-P238K = amino acids 216-447; P238K underlined; C-terminal lysine present |
| Light chain variable region IgG1- | DIQMTQSPSFLSASVGDRVTITC**KASQDVST**<br>**AVA**WYQQKPGKAPKLLIY**SASYRYT**GVPSRF<br>SGSGSGTDFTLTISSLQPEDFATYYC**QQHYS**<br>**TPWT**FGGGTKVEIK<br>(SEQ ID NO: 10) | Vk-hz2 (SEQ ID NO: 10; CDRs underlined) |
| VL-CDR1 | KASQDVSTAVA<br>(SEQ ID NO: 7) | Amino acids 24-34 of SEQ ID NO: 10 |
| VL-CDR2 | SASYRYT<br>(SEQ ID NO: 8) | Amino acids 50-56 of SEQ ID NO: 10 |
| VL-CDR3 | QQHYSTPWT<br>(SEQ ID NO: 9) | Amino acids 89-97 of SEQ ID NO: 10 |
| LC_Y12XX-hz28 | DIQMTQSPSFLSASVGDRVTITC**KASQDVST**<br>**AVA**WYQQKPGKAPKLLIY**SASYRYT**GVPSRF<br>SGSGSGTDFTLTISSLQPEDFATYYC**QQHYS**<br>**TPWT**FGGGTKVEIK*RTVAAPSVFIFPPSDEQ*<br>*LKSGTASVVCLLNNFYPREAKVQWKVDNALQ*<br>*SGNSQESVTEQDSKDSTYSLSSTLILSKADY*<br>*EKHKVYACEVTHQGLSSPVTKSFNRGEC*<br>(SEQ ID NO: 11) | CDRs underlined; CL = amino acids 108-214 (italicized) |

An "antibody" (Ab) shall include, without limitation, an immunoglobulin, which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

An "antigen binding portion" of an Ab (also called an "antigen-binding fragment") or antigen binding portion thereof refers to one or more sequences of an Ab (full length or fragment of the full length antibody) that retain the ability to bind specifically to the antigen bound by the whole Ab. Examples of an antigen-binding fragment include Fab, $F(ab')_2$, scFv (single-chain variable fragment), Fab', dsFv, sc(Fv)2, and scFv-Fc.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most, or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

As used herein, "specific binding" refers to the binding of an antigen by an antibody with a dissociation constant ($K_d$) of about 1 μM or lower as measured, for example, by surface plasmon resonance (SPR). Suitable assay systems include the BIAcore™ (GE Healthcare Life Sciences, Marlborough, MA) surface plasmon resonance system and BIAcore™ kinetic evaluation software (e.g., version 2.1).

Binding of the present antibodies to CD40 antagonizes at least one CD40 activity. "CD40 activities" include, but are not limited to, T cell activation (e.g., induction of T cell proliferation or cytokine secretion), macrophage activation (e.g., the induction of reactive oxygen species and nitric oxide in the macrophage), and B cell activation (e.g., B cell proliferation, antibody isotype switching, or differentiation to plasma cells). CD40 activities can be mediated by interaction with other molecules. "CD40 activities" include the functional interaction between CD40 and the following molecules, which are identified by their Uniprot Accession Number is parentheses:

| | |
|---|---|
| CALR | (P27797); |
| ERP44 | (Q9BS26); |
| FBL | (P22087); |
| POLR2H | (P52434); |
| RFC5 | (P40937); |
| SGK1 | (O00141); |
| SLC30A7 | (Q8NEW0); |
| SLC39A7 | (Q92504); |
| TRAF2 | (Q5T1L5); |
| TRAF3 | (Q13114); |
| TRAF6 | (Q9Y4K3); |
| TXN | (Q5T937); |
| UGGT1 | (Q9NYU2); and |
| USP15 | (Q9Y4E8). |

For example, a CD40 "activity" includes an interaction with TRAF2. CD40/TRAF2 interaction activates NF-κB and JNK. See Davies et al., Mol. Cell Biol. 25: 9806-19 (2005). This CD40 activity thus can be determined by CD40-dependent cellular NF-κB and JNK activation, relative to a reference.

As used herein, the terms "activate," "activates," and "activated" refer to an increase in a given measurable CD40 activity by at least 10% relative to a reference, for example, at least 10%, 25%, 50%, 75%, or even 100%, or more. A CD40 activity is "antagonized" if the CD40 activity is reduced by at least 10%, and in an exemplary embodiment, at least about 20%, 30%, 40%, 50%, 60%, 70%, 80%, 90%, 95%, 97%, or even 100% (i.e., no detectable activity), relative to the absence of the antagonist. For example, an antibody may antagonize some or all CD40 activity, while not activating CD40. For example, the antibody may not activate B cell proliferation. The antibody may not activate cytokine secretion by T cells, where the cytokine is at least one cytokine selected from the group consisting of IL-2, IL-6, IL-10, IL-13, TNF-α, and IFN-γ.

Variable domains may comprise one or more framework regions (FR) with the same amino acid sequence as a corresponding framework region encoded by a human germline antibody gene segment. Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Exemplary framework regions are known in the art and described in U.S. Publication No. 2020-00157233. Exemplary heavy and light variable chains for a chimeric antibody are in Table 8 of the Examples in U.S. Publication No. 2020-00157233. The isolated antibody or antigen-binding portion thereof can be a humanized antibody. Exemplary humanized heavy and light variable chains are in Table 10 of the Examples in U.S. Publication No. 2020-00157233.

Exemplary CD40 antibodies of the present invention include an isolated antibody, or antigen binding portion thereof, that specifically binds to human CD40, wherein said antibody comprises a first polypeptide portion comprising a heavy chain variable region, and a second polypeptide portion comprising a light chain variable region, wherein:

said heavy chain variable region comprises a CDR1 comprising SYWMH (SEQ ID NO: 1), a CDR2 comprising QINPTTGRSQYNEKFKT (SEQ ID NO: 2), and a CDR3 comprising WGLQPFAY (SEQ ID NO: 3); and said light chain variable region comprises a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9).

Fc Domain and Constant Region

The carboxyl-terminal "half" of a heavy chain defines a constant region (Fc) and which is primarily responsible for effector function. As used herein, the term "Fc domain" refers to the constant region antibody sequences comprising CH2 and CH3 constant domains as delimited according to Kabat et al., *Sequences of Immunological Interest*, $5^{th}$ ed., U.S. Dept. Health & Human Services, Washington, D.C. (1991). The Fc region may be derived from a human IgG. In an embodiment, the Fc region may be derived from a human IgG1A heavy variable domain can be fused to an Fc domain. The carboxyl terminus of the variable domain may be linked or fused to the amino terminus of the Fc CH2 domain. Alternatively, the carboxyl terminus of the variable domain may be linked or fused to the amino terminus of a linker amino acid sequence, which itself is fused to the amino terminus of an Fc domain. Alternatively, the carboxyl terminus of the variable domain may be linked or fused to the amino terminus of a CH1 domain, which itself is fused to the Fc CH2 domain. Optionally, the protein may comprise the hinge region after the CH1 domain, in whole, or in part. Optionally an amino acid linker sequence is present between the variable domain and the Fc domain. The carboxyl terminus of the light variable domain may be linked or fused to the amino terminus of a CL domain.

An exemplary sequence for a heavy chain CH1 is amino acids 118-215 of SEQ ID NO: 5 (ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRV; SEQ ID NO: 23). An exemplary sequence for a light chain CL is amino acids 108-214 of SEQ ID NO: 11 (RTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC; SEQ ID NO: 24).

The antibody can be a fusion antibody comprising a first variable domain that specifically binds human CD40, and a second domain comprising an Fc domain.

Exemplary Fc domains used in the fusion protein can include human IgG1 domains. While human IgG heavy chain genes encode a C-terminal lysine, the lysine is often absent from endogenous antibodies as a result of cleavage in blood circulation. Antibodies having IgG heavy chains including a C-terminal lysine, when expressed in mammalian cell cultures, may also have variable levels of C-terminal lysine present (Cai et al, 2011, *Biotechnol. Bioeng.* 108(2): 404-12). Accordingly, the C-terminal lysine of any IgG heavy chain Fc domain disclosed herein may be omitted.

The isolated antibody or antigen binding portion thereof described herein can comprise a human IgG1 Fc domain comprising a mutation at Kabat position 238 that reduces binding to Fc-gamma-receptors (FcγRs), wherein proline 238 (P238) is mutated to one of the residues selected from the group consisting of lysine (K), serine (S), alanine (A), arginine (R) and tryptophan (W), and wherein the antibody or antigen binding portion thereof has reduced FcγR binding. The isolated antibody or antigen binding portion thereof described herein can have P238 mutated to lysine in a human IgG1 Fc domain.

The isolated antibody or antigen binding portion thereof comprises an Fc domain, which comprises an amino acid sequence selected from: SEQ ID NOs: 13-20.

Exemplary sequences comprising the IgG1 Fc domains above include: SEQ ID NO: 5, SEQ ID NO: 6, SEQ ID NO: 21, and SEQ ID NO: 22.

The isolated antibody or antigen binding portion thereof disclosed herein may be Y12XX-hz28-P238K having a) a heavy chain of SEQ ID NO: 5 or 6, and b) a light chain of SEQ ID NO: 11.

In a specific embodiment, the method of the present disclosure comprises administering BMS-986325. The amino acid sequences of the heavy chain and the light of BMS-986325 are depicted in FIG. 1. Thus, in a specific embodiment, the method comprise administering an isolated antibody or antigen binding portion thereof having a heavy chain of SEQ ID NO: 5 and a light chain of SEQ ID NO: 11. BMS-986325 comprises the CDRs of humanized antibody Y12XX-hz28 (Vh-hz14; Vk-hz2) and a human IgG1 Fc domain comprising a lysine at Kabat position 238 (P238K).

BMS-986325 is an IgG1 isotype antibody containing a novel P238K mutation, that was engineered to abrogate FcγR binding to eliminate Fc-mediated signaling. As with other IgG molecules, BMS-986325 consists of two HCs and two LCs covalently bound by disulfide bonds. The resulting protein consists of a total of 1320 amino acid residues and has a molecular weight of 144,867 Da. The P238K mutation is located in the lower hinge region of the IgG1 constant domain as indicated in the primary sequence.

In nonclinical studies, the binding of BMS-986325 to CD40 from mouse, human, and cynomolgus monkey as well as to various FcγRs has been evaluated by surface plasmon resonance (SPR). BMS-986325 has also been examined in assays for CD40 antagonism on both B cells and monocyte-derived dendritic cells (iDC). BMS-986325 has also been evaluated for antagonism on isolated B cells as well as WB B cells from cynomolgus monkeys. In addition, the lack of any agonist signal was confirmed in assays on both human and cynomolgus B cells as well as human immature DCs. A highly sensitive CD40-NFκB reporter assay was used to further confirm lack of any agonist activity of BMS-986325. The summary of the in vitro and in vivo data is presented in FIGS. 2A-2C and FIG. 3, respectively The antibody or antigen binding portion thereof disclosed herein, wherein the antigen binding portion is selected from the group consisting of Fv, Fab, F(ab')2, Fab', dsFv, scFv, sc$(Fv)_2$, diabodies, and scFv-Fc.

The antibody or antigen binding portion thereof disclosed herein can be an immunoconjugate, wherein the antibody or antigen-binding portion thereof is linked to a therapeutic agent.

The antibody or antigen-binding portion thereof disclosed herein can be a bispecific antibody, wherein the antibody or antigen-binding portion thereof is linked to a second functional moiety having a different binding specificity than said antibody or antigen binding portion thereof.

The antibody or antigen binding portion thereof disclosed herein can further comprise an additional moiety.

The variable regions of the present antibodies may optionally be linked to the Fc domain by an "amino acid linker" or "linker." For example, the C-terminus of a variable heavy chain domain may be fused to the N-terminus of an amino acid linker, and an Fc domain may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include GGGGS (SEQ ID NO: 25), and a linker comprising 2, 3, 4, or 5 copies of GGGGS (SEQ ID NOs: 26 to 29, respectively). Table 3 lists suitable linker sequences for use in the present disclosure.

TABLE 3

| Representative Linker Sequences | |
|---|---|
| GGGGS | SEQ ID NO: 25 |
| $(GGGGS)_2$ | SEQ ID NO: 26 |
| $(GGGGS)_3$ | SEQ ID NO: 27 |
| $(GGGGS)_4$ | SEQ ID NO: 28 |
| $(GGGGS)_5$ | SEQ ID NO: 29 |
| AST | SEQ ID NO: 30 |
| TVAAPS | SEQ ID NO: 31 |
| TVA | SEQ ID NO: 32 |
| ASTSGPS | SEQ ID NO: 33 |

Antibody Preparation

The antibody can be produced and purified using ordinary skill in a suitable mammalian host cell line, such as CHO, 293, COS, NSO, and the like, followed by purification using one or a combination of methods, including protein A affinity chromatography, ion exchange, reverse phase techniques, or the like.

As well known in the art, multiple codons can encode the same amino acid. Nucleic acids encoding a protein sequence thus include nucleic acids having codon degeneracy. The polypeptide sequences disclosed herein can be encoded by a variety of nucleic acids. The genetic code is universal and well known. Nucleic acids encoding any polypeptide sequence disclosed herein can be readily conceived based on conventional knowledge in the art as well as optimized for production. While the possible number of nucleic acid sequence encoding a given polypeptide is large, given a standard table of the genetic code, and aided by a computer, the ordinarily skilled artisan can easily generate every possible combination of nucleic acid sequences that encode a given polypeptide.

A representative nucleic acid sequence encoding the heavy chain variable domain of BMS-986325 including a constant region CH1 and Fc domain IgG1-P238K is:

(SEQ ID NO: 34)

```
ATGAGGGCTT GGATCTTCTT TCTGCTCTGC CTGGCCGGGA
GAGCGCTCGC ACAGGTGCAG CTGGTGCAGT CTGGTGCCGA
GGTCAAAAAG CCAGGCTCCA GCGTGAAGGT GAGCTGCAAG
GCCTCTGGCT ACGCTTTCAC CTCTTATTGG ATGCACTGGG
TGAGACAGGC TCCTGGACAG GGCCTGGAGT GGATGGGCCA
GATCAACCCA ACCACCGGCA GAAGCCAGTA CAATGAGAAG
TTTAAGACCC GCGTGACCAT CACAGCCGAC AAGTCCACCA
GCACAGCTTA TATGGAGCTG TCTTCCCTGA GGTCCGAGGA
TACAGCCGTG TACTATTGCG CTCGGTGGGG CCTGCAGCCT
TTCGCTTACT GGGGCCAGGG CACCCTGGTG ACAGTGAGCT
CTGCTAGCAC CAAGGGCCCA TCGGTCTTCC CCCTGGCACC
CTCCTCCAAG AGCACCTCTG GGGGCACAGC GGCCCTGGGC
TGCCTGGTCA AGGACTACTT CCCCGAACCG GTGACGGTGT
CGTGGAACTC AGGCGCCCTG ACCAGCGGCG TGCACACCTT
CCCGGCCGTC CTACAGTCCT CAGGACTCTA CTCCCTCAGC
AGCGTGGTGA CCGTGCCCTC CAGCAGCTTG GGCACCCAGA
CCTACATCTG CAACGTGAAT CACAAGCCCA GCAACACCAA
GGTGGACAAG AGAGTTGAGC CCAAATCTTG TGACAAAACT
CACACATGCC CACCGTGCCC AGCACCTGAA CTCCTGGGGG
GAAAGTCAGT CTTCCTCTTC CCCCCAAAAC CCAAGGACAC
CCTCATGATC TCCCGGACCC CTGAGGTCAC ATGCGTGGTG
GTGGACGTGA GCCACGAAGA CCCTGAGGTC AAGTTCAACT
GGTACGTGGA CGGCGTGGAG GTGCATAATG CCAAGACAAA
GCCGCGGGAG GAGCAGTACA ACAGCACGTA CCGTGTGGTC
AGCGTCCTCA CCGTCCTGCA CCAGGACTGG CTGAATGGCA
AGGAGTACAA GTGCAAGGTC TCCAACAAAG CCCTCCCAGC
CCCCATCGAG AAAACCATCT CCAAAGCCAA AGGGCAGCCC
CGAGAACCAC AGGTGTACAC CCTGCCCCCA TCCCGGGATG
AGCTGACCAA GAACCAGGTC AGCCTGACCT GCCTGGTCAA
AGGCTTCTAT CCCAGCGACA TCGCCGTGGA GTGGGAGAGC
AATGGGCAGC CGGAGAACAA CTACAAGACC ACGCCTCCCG
```

-continued

```
TGCTGGACTC CGACGGCTCC TTCTTCCTCT ACAGCAAGCT
CACCGTGGAC AAGAGCAGGT GGCAGCAGGG GAACGTCTTC
TCATGCTCCG TGATGCATGA GGCTCTGCAC AACCACTACA
CGCAGAAGAG CCTCTCCCTG TCTCCGGGTT GA.
```

In this sequence, nucleotides 1-51 encode a signal peptide (optional), nucleotides 52-402 encode the heavy chain variable region in which nucleotides 141-155 encode CDR1, nucleotides 198-249 encode CDR2, and nucleotides 346-369 encode CDR3 of the Y12XX variable domain of the heavy chain. Nucleotides 403-696 encode a CH1 domain, and nucleotides 697-1399 encode IgG1-P238K. Nucleotides 1400-1402 are a stop codon.

A representative nucleic acid sequence encoding the light chain variable domain of BMS-986325 including a constant region CL is:

(SEQ ID NO: 35)

```
ATGAGGGCTT GGATCTTCTT TCTGCTCTGC CTGGCCGGGC
GCGCCTTGGC CGACATCCAG ATGACCCAGT CCCCCTCCTT
CCTGTCTGCC TCCGTGGGCG ACAGAGTGAC CATCACCTGT
AAGGCTTCCC AGGATGTGAG CACAGCCGTG GCTTGGTACC
AGCAGAAGCC AGGCAAGGCC CCCAAGCTGC TGATCTATTC
CGCCTCTTAC AGGTATACCG GCGTGCCCTC TCGGTTCTCC
GGCAGCGGCT CTGGCACAGA CTTTACCCTG ACAATCTCCA
GCCTGCAGCC TGAGGATTTC GCCACCTACT ATTGCCAGCA
GCACTACTCC ACCCCATGGA CATTTGGCGG CGGCACCAAG
GTGGAGATCA AGCGTACGGT GGCTGCACCA TCTGTCTTCA
TCTTCCCGCC ATCTGATGAG CAGTTGAAAT CTGGAACTGC
CTCTGTTGTG TGCCTGCTGA ATAACTTCTA TCCCAGAGAG
GCCAAAGTAC AGTGGAAGGT GGATAACGCC CTCCAATCGG
GTAACTCCCA GGAGAGTGTC ACAGAGCAGG ACAGCAAGGA
CAGCACCTAC AGCCTCAGCA GCACCCTGAC GCTGAGCAAA
GCAGACTACG AGAAACACAA AGTCTACGCC TGCGAAGTCA
CCCATCAGGG CCTGAGCTCG CCCGTCACAA AGAGCTTCAA
CAGGGGAGAG TGTTAG.
```

In this sequence, nucleotides 1-51 encode a signal peptide (optional), nucleotides 52-372 encode the light chain variable region in which nucleotides 121-153 encode CDR1, nucleotides 199-219 encode CDR2, and nucleotides 316-342 encode CDR3. Nucleotides 373-693 encode a CL. Nucleotides 694-696 are a stop codon The coding sequence for the heavy and/or light chain optionally may encode a signal peptide, such as MRAWIFFLLCLAGRALA (SEQ ID NO: 36), at the 5' end of the coding sequence. As described above, an exemplary nucleic acid coding sequence for this signal peptide is (SEQ ID NO: 37)

```
ATGAGGGCTT GGATCTTCTT TCTGCTCTGC CTGGCCGGGA
GAGCGCTCGC A.
```

Accordingly, a nucleic acid encoding an antibody disclosed herein is also contemplated. Such a nucleic acid may be inserted into a vector, such as a suitable expression vector, e.g., pHEN-1, for expression in an isolated cell (Hoogenboom et al. (1991) *Nucleic Acids Res.* 19: 4133-4137). Further provided is an isolated host cell comprising the vector and/or the nucleic acid.

The antibody of the disclosure can be produced and purified using only ordinary skill in any suitable mammalian host cell line, such as CHO (Chinese hamster ovary cells), 293 (human embryonic kidney 293 cells), COS cells, NSO cells, and the like, followed by purification using one or a combination of methods, including protein A affinity chromatography, ion exchange, reverse phase techniques, or the like.

Pharmaceutical Compositions and Methods of Treatment

A pharmaceutical composition comprises a therapeutically-effective amount of one or more antibodies and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are known in the art. See, e.g., Remington, The Science and Practice of Pharmacy, A. Gennaro, et al., eds., 21st ed., Mack Publishing Co. (2005).

In an embodiment, a pharmaceutical composition comprises an antibody or antigen-binding portion thereof described herein in a formulation comprising histidine, sucrose, pentetic acid and polysorbate. In an embodiment, the formulation comprising 150 mg/ml antibody, 20 mM histidine, 250 mM sucrose, 50 micromolar pentetic acid and 0.05% (w/v) polysorbate 80, pH 6.0. The formulation may be buffered with a sodium acetate buffer or a sodium phosphate buffer. In an embodiment, the pharmaceutical composition comprises or consists of 150 mg/ml BMS-986325, 20 mM histidine, 250 mM sucrose, 50 micromolar pentetic acid and 0.05% (w/v) polysorbate 80, pH 6.0.

The pharmaceutical composition may be administered alone or in combination therapy, (i.e., simultaneously or sequentially) with an immunosuppressive/immunomodulatory and/or anti-inflammatory agent. An exemplary type of agent is a cytotoxic T lymphocyte-associated protein 4 (CTLA4) mutant molecule. An exemplary CTLA4 mutant molecule is L104EA29Y-Ig (belatacept) which is a modified CTLA4-Ig. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

A method of treating an autoimmune disease in a patient in need of such treatment may comprise administering to the patient a therapeutically effective amount of the antibody, or antigen binding portion thereof, as described herein. Also provided herein is the use of an antibody, or antigen-binding portion thereof or treating an autoimmune disease in a patient in need of such treatment and/or for treating or preventing an autoimmune disease in a patient in need of such treatment, that may comprise administering to the patient a therapeutically effective amount of the antibody, or antigen binding portion thereof. Antagonizing CD40-mediated T cell activation could inhibit undesired T cell responses occurring during autoimmunity. Inhibiting CD40-mediated T cell activation could moderate the progression and/or severity of these diseases.

The use of an antibody, or antigen-binding portion thereof, of the disclosure, in the preparation of a medicament for treating or preventing an autoimmune disease in a patient in a patient in need of such treatment, is also provided. The medicament can, for example, be administered in combination with an immunosuppressive/immunomodulatory and/or anti-inflammatory agent.

As used herein, a "patient" means an animal, e.g., mammal, including a human. In the method disclosed herein, the patient may be diagnosed with an autoimmune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, inflammation, allergy, autoimmune disease, or graft-related disease. In the present application, the method is directed to treatment of an autoimmune disease. An "autoimmune disease" refers to any disease associated with the development of an autoimmune reaction in an individual, including a cellular and/or a humoral immune reaction. An example of an autoimmune disease is Sjögren's syndrome. Treatment of primary Sjögren's syndrome (pSS) as well as secondary Sjögren's syndrome is encompassed. Other autoimmune diseases include inflammatory bowel disease (IBD) including, but not limited to ulcerative colitis and Crohn's disease, systemic lupus erythematosus (SLE), lupus nephritis, multiple sclerosis (MS), rheumatoid arthritis (RA), diabetes, psoriasis, scleroderma, and atherosclerosis.

The pharmaceutical composition may be administered alone or as a combination therapy, (i.e., simultaneously or sequentially) with an immunosuppressive/immunomodulatory and/or anti-inflammatory agent. Different autoimmune diseases can require use of specific auxiliary compounds useful for treating autoimmune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

Any suitable method or route can be used to administer the antibody, or antigen-binding portion thereof, or the pharmaceutical composition. Routes of administration include, for example, intravenous (IV), intraperitoneal, subcutaneous (SC), or intramuscular administration. In an embodiment, the antibody, or antigen binding portion thereof, or the pharmaceutical composition is administered subcutaneously or intravenously.

The frequency of administration depends on numerous factors including, for example, the type and severity of the autoimmune disease being treated, the use of combination therapy, the route of administration of the antibody, or antigen binding portion thereof, or pharmaceutical composition, and the weight of the patient. The antibody polypeptide can be administered daily, weekly, biweekly (once every 2 weeks), every 2-3 weeks, every 3-4 weeks, or monthly.

The duration of treatment similarly depends on numerous factors. Treatment can comprise a single dose, or one or more doses. Treatment can be administered regularly over weeks, months, or years, or sporadically on an as-needed basis.

Dosage regimens are adjusted to provide the optimum desired response (e.g., a therapeutic response). For example, a single bolus may be administered, several divided doses may be administered over time, or the dose may be proportionally reduced, or increased as needed in response to the treatment. Formulating pharmaceutical compositions for use in intravenous (IV), intraperitoneal, subcutaneous (SC), or intramuscular administration in dosage unit form is useful for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective dose of administered antibody depends on numerous factors, including, for example, the type and severity of the autoimmune disease being treated, the use of combination therapy, the route of administration of the antibody, or antigen binding portion thereof, or pharmaceutical composition, and the weight of the patient. A non-limiting range for a therapeutically effective amount of the anti-CD40 monoclonal antibody is 0.1-20 milligram/kilogram (mg/kg), and in an aspect, 1-10 mg/kg, relative to the body weight of the patient.

A non-limiting range for a therapeutically effective amount of the anti-CD40 monoclonal antibody wherein the heavy chain variable region comprises (i) a CDR1 comprising SYWMH (SEQ ID NO: 1), a CDR2 comprising QINPTTGRSQYNEKFKT (SEQ ID NO: 2), and a CDR3 comprising WGLQPFAY (SEQ ID NO: 3), and the light chain variable region comprises a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9); and (ii) a human IgG1 Fc domain comprising a mutation at Kabat position 238 that reduces binding to Fc-gamma-receptors (FcγRs), is from 0.3 milligram (mg) to 1000 mg for intravenous (IV) administration and from 100 mg to 1000 milligram for subcutaneous (SC) administration.

In an embodiment, the administration may be intravenous (IV) and the dose is from 0.3 to 1000 milligrams (mg) of the antibody polypeptide. The dose may be selected from 0.3, 1, 3, 10, 30, 100, 150, 300, 600, or 1000 mg of the antibody polypeptide. The method may comprise more than one iteration of the administering step. The method may comprise intravenous (IV) administration, where the dose is from 100 to 600 mg of the antibody polypeptide, and the method comprises at least four iterations of the administering step. In an embodiment, dosing is once a week (QW) for at least four iterations of the administering step. For instance, a dose of 100 mg, 150 mg, 200 mg, or 300 mg is administered on week for at least four iterations. In another embodiment, dosing is once every two weeks (q2wk) with at least two iterations of the administering step. For instance, a dose of 200 mg, 300 mg, 400 mg, or 600 mg is administered every two weeks to the patient for at least two iterations. In an embodiment, the initial dose is higher that the subsequent doses. For instance, the initial dose is 300 mg and subsequent doses are 100 mg.

Exemplary intravenous (IV) doses include, but are not limited to, 0.1 mg, 0.5 mg, 0.8, 1 mg, 3, mg, 10 mg, 30 mg, 50 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 320 mg, 340 mg, 360 mg, 380 mg, 400 mg, 420 mg, 440 mg, 460 mg, 480 mg, 500 mg, 520 mg, 540 mg, 560 mg, 580 mg, 600 mg, 620 mg, 640 mg, 660 mg, 680 mg, 700 mg, 750 mg, 800 mg, 850 mg, 900 mg, 950 mg, and 1000 mg of antibody polypeptide. Exemplary IV doses include, but are not limited to, 80 mg, 90 mg, 100 mg, 200 mg, 300 mg, 400 mg, 500 mg, 600 mg, 700 mg, 800 mg, 900 mg, and 1000 mg of antibody polypeptide. In an embodiment, the antibody is BMS 986325. In an embodiment, the IV dose is 75 to 100 mg, or 90 mg. In an embodiment, the IV dose is 75 to 100 mg, or 90 mg administered weekly (qwk). In an embodiment, an IV dose is 75 to 100 mg, or 90 mg is administered weekly (qwk) for at least 4 weeks. In an embodiment, the IV dose is 75 to 100 mg, or 90 mg of BMS 986325. In an embodiment, the IV dose is 75 to 100 mg, or 90 mg of BMS 986325 administered weekly (qwk). In an embodiment, an IV dose is 75 to 100 mg, or 90 mg of BMS 986325 is administered weekly (qwk) for at least 4 weeks. In an embodiment, an IV dose is 150 to 200 mg, or 180 mg of BMS 986325 is administered every other week for at least 4 weeks.

In an embodiment, the administration is subcutaneous (SC) and the dose is from 100 to 1000 mg of the antibody polypeptide. The dose may be selected from 100 mg, 300 mg, 600 mg, or 1000 mg of the antibody polypeptide. The method may comprise more than one iteration of the administering step. The method may comprise sub-cutaneous administration, where the dose is selected from 100 mg to 600 mg, such as 100 mg, 300 mg or 600 mg of the antibody polypeptide. In an embodiment, the initial dose is higher than the subsequent doses.

Exemplary ranges for SC doses include, but are not limited to, 50 mg to 1000 mg, 50 mg to 750 mg, 75 mg to 700 mg, 100 mg to 1000 mg, 100 mg to 600 mg, 150 mg to 1000 mg, 150 mg to 600 mg, 300 mg to 600 mg, 100 mg to 150 mg to 300 mg SC, and 150 mg to 300 mg to 600 mg SC of the antibody. SC doses include, but are not limited to, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 350 mg, 400 mg, 450 mg, 500 mg, 550 mg, 600 mg, and 1000 mg of antibody polypeptide. Exemplary SC doses include, but are not limited to, 100 mg, 150 mg, 240 mg, 250 mg, 300 mg, and 600 mg of antibody polypeptide. In an embodiment, the antibody is BMS 986325. In an embodiment, the SC dose is 200 to 300 mg or 240 mg. In an embodiment, the SC dose is 200 to 300 mg or 240 mg administered one every two weeks (q2wk). In an embodiment, an SC dose of 100 mg is administered weekly for at least 4 weeks, or an SC dose of 300 mg is administered weekly for at least 4 weeks, or an SC dose of 600 mg is administered weekly for at least 4 weeks. In an embodiment, the SC dose of BMS 986325 is 200 to 300 mg or 240 mg. In an embodiment, the SC dose is 200 to 300 mg or 240 mg of BMS 986325 administered one every two weeks (q2wk). In another embodiment, an SC dose of 100 mg of BMS 986325 is administered weekly for at least 4 weeks, or an SC dose of 300 mg of BMS 986325 is administered weekly for at least 4 weeks, or an SC dose of 600 mg of BMS 986325 is administered weekly for at least 4 weeks, or an SC dose of 600 mg of BMS 986325 is administered once every other week for at least 4 weeks.

The dose of antibody polypeptide(s) can be further guided by the amount of antibody polypeptide(s) required for CD40 antagonism in in vitro and/or in vivo models of disease states. Representative models are described in the examples.

Kits

A kit useful for treating an autoimmune disease such as Sjögren's syndrome in a human patient is provided. The kit can comprise (a) a dose of an antibody, or antigen binding portion thereof of the present disclosure, and (b) instructional material for using the antibody, or antigen binding portion thereof, in the method of treating an immune disease, or for using the antibody, or antigen binding portion thereof, in the method of treating or preventing an autoimmune or inflammatory disease, in a patient. For example, the antibody, or antigen-binding portion thereof can be BMS 986325. In an embodiment, the dose ranges from 1 milligram (mg) to 1000 mg. In an embodiment, the dose of antibody BMS-986325 is a formulation comprising 20 mM histidine, 250 mM sucrose, 50 micromolar pentetic acid and 0.05% (w/v) polysorbate 80, pH 6.0. The formulation may comprise a sodium acetate buffer or a sodium phosphate buffer.

"Instructional material," as that term is used herein, includes a publication, a recording, a diagram, or any other medium of expression, which can be used to communicate the usefulness of the composition and/or compound of the invention in a kit. The instructional material of the kit may, for example, be affixed to a container or contained within the confines of the kit or the container, which contains the compound and/or composition of the invention or be shipped together with a container, which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

EXAMPLES

Example 1: Kinetics of Binding to Human and Cyanomolgus CD40

The kinetics and affinity of BMS-986325 binding to human CD40 and cynomolgus CD40 were characterized by surface plasmon resonance (SPR), by capturing BMS-986325 on an immobilized protein A sensor chip surface and testing the binding of multiple concentrations of monomeric human CD40 or cynomolgus CD40 analyte. BMS-986325 was found to bind to human CD40 with a dissociation constant (Kd) of 5.3 nM, and to cynomolgus CD40 with a Kd of 6.7 nM. See Table 4. BMS-986325 was also tested for binding to murine CD40 and rat CD40 in a single-cycle kinetic SPR assay, where BMS-986325 demonstrated strong binding to the human CD40 and cynomolgus CD40 surfaces; no detectable binding to either murine CD40 or rat CD40 was observed (data not shown).

TABLE 4

Determination of CD40 Target-binding Properties of BMS-986325 by Surface Plasmon Resonance

| Target | ka (1/Ms) | kd (1/s) | Kd (nM) |
|---|---|---|---|
| Human CD40 | $2.3 \times 10^5$ | $1.2 \times 10^{-3}$ | 5.3 |
| Cynomolgus CD40 | $2.4 \times 10^5$ | $1.6 \times 10^{-3}$ | 6.7 |

Example 2: Binding to FcγRs

BMS-986325 comprises a novel IgG1-P238K isotype, which was engineered to reduce FcγR binding and FcγR2; or cynomolgus FcγRs (cyCD32a, cyCD32b, cyCD16. See Table 5. Further, binding of BMS-986325 to the high-affinity human CD64 or cynomolgus CD64 FcγRs was more than 100-fold weaker than binding of wild-type human IgG1 control. See Table 5.

TABLE 5

FcγR Binding Properties of BMS-986325

| FcγR | IgG1 Kd (nM) | BMS-986325 Kd (nM) |
|---|---|---|
| hCD64 | <0.1 | 17 |
| hCD32a-H131 | 446 | NB |
| hCD32a-R131 | 665 | NB |
| hCD32b | 3,090 | NB |
| hCD16a-V158 | 119 | NB |
| hCD16a-F158 | 4,430 | NB |
| cyCD64 | <0.1 | 13 |
| cyCD32a | 1,520 | NB |
| cyCD32b | 877 | NB |
| cyCD16 | 164 | NB |

Abbreviations: NB, no detectable binding.

Example 3: Summary of Non-Clinical Pharmacokinetics Evaluation of BMS-986325

The pharmacokinetics (PK) of BMS-986325 (Y12XX-hz28-P238K) were evaluated in mice and cynomolgus monkeys. Since BMS-986325 does not cross react to murine CD40 receptors, the PK evaluated in mice is intrinsic or non-specific PK. BMS-986325 cross reacts with monkey CD40 receptors, therefore the total PK (specific and non-specific PK) was evaluated in monkeys. After intravenous (IV) administration of BMS-986325 (single 1- and 10-mg/kg doses) to mice, BMS-986325 exhibited low total serum clearance "CLT" of 0.5 to 1.02 mL/d/kg, limited volume of distribution at steady state "Vss" of 0.12 to 0.19 L/kg, and long apparent elimination half-life "T-HALF" of 118 to 183 hours (~5 to 8 days).

In monkeys, a single subcutaneous (SC) dose (10 mg/kg) of BMS-986325 was administered. The dose administered is a dose at which specific clearance (target-mediated drug disposition "TMDD") is not saturated. After the single SC dose, BMS-986325 was well absorbed, with an absolute bioavailability of 70.4% (relative to exposures at the same IV dose). After IV administration of BMS-986325 (10 mg/kg single dose) to monkeys, BMS-986325 exhibited a CLT of 0.41 mL/d/kg, a limited Vss of 0.05 L/kg, and a T-HALF of 100 hours (~4 days). The time to maximum plasma concentration "Tmax" following a single SC dose of BMS-986325 (doses of 1, 10, and 100 mg/kg administered) to monkeys was 24 to 54 hours. There were more-than-dose-proportional increases in exposure (maximum concentration "Cmax" and area under the concentration vs time curve extrapolated from time zero to infinity "AUC[INF]") and an increase in T-HALF with dose (~31, ~119, and ~197 hours at 1, 10, and 100 mg/kg dose, respectively). These data suggest non-linear PK and a saturable clearance mechanism; this likely results from target (CD40)-mediated clearance, reflecting TMDD. In this single-dose PK study, anti-drug antibody (ADA) formation was detected in ~50% of monkeys, but had no apparent impact on the overall PK parameters.

Pharmacokinetic/pharmacodynamic modeling TMDD model with quasi steady-state assumption (TMDD-Qss) was used to describe the nonlinear PK observed in monkeys, establish a relationship between serum drug exposure and CD40 receptor occupancy (RO) and subsequent human dose projection.

Example 4: Pharmacokinetic/Pharmacodynamic Modeling of Data from Single-dose Study in Monkeys (Study DN18016) and Projection of Human Pharmacokinetics and Efficacious Dose PK/PD modeling was used to describe the nonlinear PK observed in monkeys and establish a relationship between serum drug exposure and CD40 RO. BMS-986325 exhibited nonlinear PK (greater-than-dose-proportional increases in exposure and an increase in T-HALF with dose), which are characteristics of a saturable clearance mechanism resulting from TMDD. To describe the nonlinear PK of BMS-986325 observed in monkeys, a target-mediated drug disposition model with quasi steady-state assumption (TMDD-Qss model) was used to account for nonspecific (linear), and specific or CD40 target-mediated (nonlinear) clearance processes. The drug concentrations and RO data from monkeys were simultaneously fitted to the PK/PD model. The model-fitted curves described both the PK and RO profiles, demonstrating that the CD40 receptor-mediated binding and disposition are responsible for the nonlinear PK of BMS-986325.

The human PK of BMS-986325 was predicted using the same PK/PD model used to describe the PK and RO of BMS-986325 in monkeys. To predict human PK parameters, the CLT, Vss, and T-HALF of BMS-986325 in monkeys in the absence of TMDD were calculated. For the nonspecific elimination or linear clearance component, the model-derived nonspecific clearance in monkeys (0.34 mL/h/kg) was allometrically scaled to that in humans (0.23 mL/h/kg) using an exponent of 0.85. The human Vss (0.08 L/kg) was also allometrically predicted from monkey data (0.08 L/kg) using an exponent of 1. The T-HALF in human was calculated to be 13 days (10 days in monkeys). The TMDD in humans was assumed to be same as in monkeys. The bioavailability of BMS-986325 after SC administration in humans was assumed to be the same as in monkeys.

Assuming the same PK/PD relationship exists between monkey and human, and based on estimated human PK parameters and steady-state trough plasma concentrations of 0.03 to 0.4 μM, the efficacious doses of BMS-986325 to achieve RO of 90%, 95%, and 99% in humans were projected (Table 6). Complete KLH-mediated TDAR suppression was achieved at RO of >95% with BMS-986325 in monkeys and BMS-986090 in humans.

TABLE 6

Projected Human Efficacious Doses of BMS-986325 in Humans

| Receptor Occupancy | Projected Efficacious SC Dose of BMS-986325 in Humans[a] Every-week | Every-2-weeks |
|---|---|---|
| 90% | 66 mg | 275 mg |
| 95% | 90 mg | 240 mg |
| 99% | 180 mg | 775 mg |

[a]In a 70-kg normal healthy human subject.

Example 5: Clinical Study of BMS-986325 in Human Subjects

The clinical trial protocol entitled "Clinical Protocol IM039-004 A Double-Blind, Placebo-Controlled, Randomized, Single and Multiple Dose Study on the Safety, Pharmacokinetics and Pharmacodynamics of Subcutaneous and Intravenous BMS-986325 Administration in Healthy Participants and Participants with Primary Sjögren's Syndrome" describes in detail a clinical trial protocol and is appended to the present application. Excerpts of the protocol are provided below.

To date, BMS-986325 has not been administered to humans. The proposed First-in-Human (FIH) study for BMS-986325 will include single- and multiple-ascending dose (SAD and MAD), placebo-controlled cohorts of healthy participants (Parts A and B) and cohorts of participants with primary Sjögren's syndrome (Part C), via IV and/or SC administration routes under a combined protocol. The objective of this initial study is to evaluate the safety, tolerability, PK, PD (e.g., biomarker response), immunogenicity, bioavailability and disease effects of BMS-986325, using doses and duration of dosing guided by the initial toxicology program, and by data emerging from the study itself.

The proposed SAD starting dose and top dose is 0.3 mg and 1000 mg, respectively, supported by minimum anticipated biological effect level (MABEL), pharmacologically active dose (PAD), and NOAEL approaches. Dose escalation decisions will be based on evaluation of available results from the ongoing cohorts including safety and tolerability, clinical laboratory assessments, and possibly available PK, PD, and target engagement data. If BMS-986325 exhibits a profile supportive of further development, studies in participants with select immune-mediated diseases would be planned.

Human Dosing Range and Safety Margins

The Phase 1 FIH study of BMS-986325 (SAD and MAD) is proposed to be evaluated in healthy participants (Parts A and B) and in participants with Sjögren's syndrome (Phase 1b, Part C). The proposed dose ranges to be evaluated in the SAD portion of the study (Part A) are 0.3-1000 mg (9 dose levels) IV (see FIG. 4). In the MAD portion of the study (Part B), weekly SC injections of 100, 300, and 600 mg administered for 4 weeks will be evaluated. Dosing in Part C will not exceed safe exposure in SAD/MAD, with duration of dosing limited to 4 weeks and frequency of dosing not more than once weekly.

Selection of BMS-986325 Starting Dose for the FIH Study

The primary objective of the FIH clinical study (IM039-004) is to characterize the safety and tolerability of SAD and MAD doses of BMS-986325 in healthy participants (Parts A and B), and multiple doses in participants with Sjögren's syndrome (Part C).

To select the starting dose, both MABEL ("minimum anticipated biological effect level") and NOAEL ("no observed adverse effect dose level") approaches were employed. The MABEL dose was defined as a dose at which the maximum CD40 RO in human WB is approximately 40%. The starting dose of 0.3 mg IV is projected to provide CD40 RO of 39.5% at Cmax. At this RO level, the pharmacological activity is anticipated to be minimal based on results from ex vivo CD40L-driven B-cell activation (CD86) assay and KLH-induced TDAR in the single-dose PK/PD study in cynomolgus monkeys. Additionally, previous experience in the clinic with anti-CD40 dAb BMS-986090 demonstrated a maximum RO achievement of 8% and 42% at 3 and 10 mg SC doses, respectively. As neither RO coverages resulted in an inhibition of TDAR (T-cell-dependent antibody responses), it is highly unlikely the proposed starting dose of 0.3 mg IV, which is projected to provide an RO of 39.5% (at Cmax), would trigger any TDAR suppression.

The 1-month toxicity study in monkeys at weekly doses of up to 100 mg/kg (IV) showed that BMS-986325 was well tolerated at all doses with effects consistent with its pharmacology. See FIG. 5. Based on the results of that study, the NOAEL was considered to be 100 mg/kg IV. The predicted Cmax and AUC(INF) (area under the concentration versus time curve extrapolated from time zero to infinity after IV administration of the starting dose (0.3 mg) are 0.09 μg/mL and 0.57 μg·h/mL, respectively, based on predicted human PK (FIG. 5). The starting dose of 0.3 mg BMS-986325 IV is projected to provide an exposure safety margin that is 1,192,982-fold below the assessed NOAEL in terms of AUC and 26,111-fold below for Cmax (FIG. 5).

Selection of Top Dose and Dose Range

The proposed top dose in SAD is 1000 mg administered as IV infusion. The dose needs be tested in case significant TMDD is observed in patients with immune-mediated disease, which may require loading dose in future studies, as shown in Phase 2a study of iscalimab in patients with primary Sjögren's syndrome. The dose of 1000 mg BMS-986325 IV is projected to provide a CD40 RO of 99% (at Cmax) and an exposure that is 6- and 14-fold by Cmax and AUC, respectively, below the NOAEL exposure (100 mg/kg/week) assessed in the 1-month monkey toxicology study. See FIG. 5.

The efficacious human dose is predicted to be 90 mg qwk or 240 mg q2wk for maintaining a trough RO of >95%, assuming the same PK profile in participants with Sjögren's syndrome as in healthy participants. The SAD dose escalation scheme and the corresponding predicted human PK, RO and safety multiples based on NOAEL and MABEL approach are summarized in FIG. 4.

Overall, the proposed doses for this study will span the anticipated efficacious dose-range projected for meaningful PD effects and are considered to be within an appropriate safety margin indicated by the nonclinical toxicology results. Dose escalation decisions for the SAD study will depend on a thorough evaluation of the safety, tolerability (including reported AEs, findings from physical examinations, clinical laboratory results, vital signs, ECGs and safety PD biomarkers), and any available PK and RO data for each dose cohort.

Although the present embodiments have been described in detail with reference to examples above, it is understood that various modifications can be made without departing from the spirit of these embodiments, and would readily be known to the skilled artisan.

These and other aspects disclosed herein, including the exemplary specific treatment methods, medicaments, and uses listed herein, will be apparent from the teachings contained herein.

What is claimed is:

1. A method of treating Sjögren's syndrome in a human patient, the method comprising administering to the patient in need thereof an antibody, or antigen-binding portion thereof, that specifically binds to human CD40, wherein the antibody or antigen-binding portion thereof comprises a first polypeptide portion comprising a heavy chain variable region, and a second polypeptide portion comprising a light chain variable region, wherein:

the heavy chain variable region comprises a CDR1 comprising SYWMH (SEQ ID NO: 1), a CDR2 comprising QINPTTGRSQYNEKFKT (SEQ ID NO: 2), and a CDR3 comprising WGLQPFAY (SEQ ID NO: 3); and the light chain variable region comprises a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9), wherein the antibody, or antigen-binding portion thereof, is administered subcutaneously at a dose selected from 100 mg to 1000 mg of the antibody, or antigen-binding portion thereof, and the method comprises at least four iterations of the administering step.

2. The method of claim 1, wherein the antibody, or antigen-binding portion thereof, is in a formulation comprising histidine, sucrose, pentetic acid, and polysorbate.

3. The method of claim 1, wherein the antibody or antigen-binding portion thereof, comprises a human IgG1 Fc domain comprising a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan.

4. The method of claim 1, wherein the dose is 150 mg, 300 mg, or 600 mg of the antibody or antigen-binding portion thereof.

5. The method of claim 1, wherein the dose is 150 mg of the antibody or the antigen-binding portion thereof, administered weekly or once every 2 weeks.

6. The method of claim 1, wherein the dose is 300 mg of the antibody or the antigen-binding portion thereof, administered weekly for at least 4 weeks.

7. The method of claim 1, wherein the dose is 150 mg or 600 mg of the antibody or antigen-binding portion thereof, administered once every 2 weeks.

8. The method of claim 1, wherein the antibody or antigen-binding portion thereof, is administered in combination with an immunosuppressive/immunomodulatory and/or anti-inflammatory agent.

9. The method of claim 8, wherein the antibody or antigen-binding portion thereof, and the immunosuppressive, immunomodulatory and/or anti-inflammatory agent are administered sequentially.

10. The method of claim 8, wherein the antibody or antigen-binding portion thereof, and the immunosuppressive, immunomodulatory, and/or anti-inflammatory agent are administered simultaneously.

11. The method of claim 8, wherein the antibody or antigen-binding portion thereof, and the immunosuppressive, immunomodulatory, and/or anti-inflammatory agent are formulated in a single composition.

12. The method of claim 1, wherein the antibody, or antigen-binding portion thereof, comprises the first polypeptide portion comprising a heavy chain variable region, and the second polypeptide portion comprising a light chain variable region, wherein:

the heavy chain variable region comprises the amino acid sequence of the heavy chain variable region comprises the amino acid sequence of (SEQ ID NO: 4)
QVQLVQSGAEVKKPGSSVKVSCKASGYAFTSYWMHWVRQAPGQGLEWMGQ
INPTTGRSQYNEKFKTRVTITADKSTSTAYMELSSLRSEDTAVYYCARWG
LQPFAYWGQGTLVTVSS, and the light chain variable region comprises the amino acid sequence of (SEQ ID NO: 10)
DIQMTQSPSFLSASVGDRVTITCKASQDVSTAVAWYQQKPGKAPKLLIYS
ASYRYTGVPSRFSGSGSGTDFTLTISSLQPEDFATYYCQQHYSTPWTFGG
GTKVEIK.

13. The method of claim 1, wherein the antibody, or antigen-binding portion thereof, comprises an Fc domain which comprises an amino acid sequence selected from:

EPKSCDKTHTCPPCPAPELLGGKSVFLFPPKPKDTLMISRTPEVTCVVVDVSHEDP
EVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPG
(SEQ ID NO: 13; IgG1-P238K (-C-term Lys)), EPKSCDKTHTCPPCPAPELLGGKSVFLFPPKPKDTLMISRTPEVTCVVVDVSHEDP
EVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPG
K (SEQ ID NO: 14; IgG1-P238K),

*ASTKGPSVFPLAPSSKSTSGGTAALGCLVKDYFPEPVTVSWNSGALTSGVHTFPAVLQS*
*SGLYSLSSVVTVPSSSLGTQTYICNVNHKPSNTKVDKR*VEPKSCDKTHTCPPCPAPELLGGKS
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKS
RWQQGNVFSCSVMHEALHNHYTQKSLSLSPG (SEQ ID NO: 15; CH1-IgG1-P238K (-C-term Lys)),

*ASTKGPSVFPLAPSSKSTSGGTAALGCLVKDYFPEPVTVSWNSGALTSGVHTFPAVLQS*
*SGLYSLSSVVTVPSSSLGTQTYICNVNHKPSNTKVDKR*VEPKSCDKTHTCPPCPAPELLGGKS
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 16; CH1-IgG1-P238K),

EPKSCDKTHTCPPCPAPELLGGKSVFLFPPKPKDTLMISRTPEVTCVVVDVSHEDP
EVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSLSP
G (SEQ ID NO: 17; IgG1f-P238K (-C-term Lys)), EPKSCDKTHTCPPCPAPELLGGKSVFLFPPKPKDTLMISRTPEVTCVVVDVSHEDP
EVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSLSP
GK (SEQ ID NO: 18; IgG1f-P238K),

*ASTKGPSVFPLAPSSKSTSGGTAALGCLVKDYFPEPVTVSWNSGALTSGVHTFPAVLQS*
*SGLYSLSSVVTVPSSSLGTQTYICNVNHKPSNTKVDKR*VEPKSCDKTHTCPPCPAPELLGGKS
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKS
RWQQGNVFSCSVMHEALHNHYTQKSLSLSPG (SEQ ID NO: 19; CH1-IgG1f-P238K (-C-term Lys)), or

*ASTKGPSVFPLAPSSKSTSGGTAALGCLVKDYFPEPVTVSWNSGALTSGVHTFPAVLQS*
*SGLYSLSSVVTVPSSSLGTQTYICNVNHKPSNTKVDKR*VEPKSCDKTHTCPPCPAPELLGGKS
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 20; CH1-IgG1f-P238K).

14. The method of claim 1, wherein the antibody, or antigen-binding portion thereof, comprises:

the first polypeptide portion, which comprises or consists of the amino acid sequence of QVQLVQSGAEVKKPGSSVKVSCKASGYAFTSYWMHWVRQAPGQGLEWMGQ
INPTTGRSQYNEKFKTRVTITADKSTSTAYMELSSLRSEDTAVYYCARWG
LQPFAYWGQGTLVTVSS*ASTKGPSVFPLAPSSKSTSGGTAALGCLVKDYF*
*PEPVTVSWNSGALTSGVHTFPAVLQSSGLYSLSSVVTVPSSSLGTQTYIC*
*NVNHKPSNTKVDKRV*EPKSCDKTHTCPPCPAPELLGGKSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG
(SEQ ID NO: 5; HC_Y12XX-hz28-CH1-IgG1-P238K - no terminal lysine);

and the second polypeptide portion, which comprises or consists of the amino acid sequence of DIQMTQSPSFLSASVGDRVTITCKASQDVSTAVAWYQQKPGKAPKLLIYS
ASYRYTGVPSRFSGSGSGTDFTLTISSLQPEDFATYYCQQHYSTPWTFGG
GTKVEIK*RTVAAPSVFIFPPSDEQLKSGTASVVCLLNNFYPREAKVQWKV*
*DNALQSGNSQESVTEQDSKDSTYSLSSTLTLSKADYEKHKVYACEVTHQG*
*LSSPVTKSFNRGEC* (SEQ ID NO: 11; LC_Y12XX-hz28-CL).

15. The method of claim 1, wherein the antibody, or antigen-binding portion thereof, is antibody BMS-986325, wherein the first polypeptide portion has the amino acid sequence of QVQLVQSGAEVKKPGSSVKVSCKASGYAFTSYWMHWVRQAPGQGLEWMGQ
INPTTGRSQYNEKFKTRVTITADKSTSTAYMELSSLRSEDTAVYYCARWG
LQPFAYWGQGTLVTVSS*ASTKGPSVFPLAPSSKSTSGGTAALGCLVKDYF*
*PEPVTVSWNSGALTSGVHTFPAVLQSSGLYSLSSVVTVPSSSLGTQTYIC*
*NVNHKPSNTKVDKRV*EPKSCDKTHTCPPCPAPELLGGKSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG
(SEQ ID NO: 5; HC_Y12XX-hz28-CH1-IgG1-P238K - no terminal lysine);

and the second polypeptide portion has the amino acid sequence of

DIQMTQSPSFLSASVGDRVTITCKASQDVSTAVAWYQQKPGKAPKLLIYS
ASYRYTGVPSRFSGSGSGTDFTLTISSLQPEDFATYYCQQHYSTPWTFGG
GTKVEIK*RTVAAPSVFIFPPSDEQLKSGTASVVCLLNNFYPREAKVQWKV*
*DNALQSGNSQESVTEQDSKDSTYSLSSTLTLSKADYEKHKVYACEVTHQG*
*LSSPVTKSFNRGEC* (SEQ ID NO: 11; LC_Y12XX-hz28-CL).

16. The method of claim 15, wherein the dose of antibody, or antigen-binding portion thereof, is a formulation comprising histidine, sucrose, pentetic acid, and polysorbate 80, pH 6.0.

17. The method of claim 16, wherein the formulation comprises 20 mM histidine, 250 mM sucrose, 50 micromolar pentetic acid, and 0.05% (w/v) polysorbate 80, pH 6.0.

* * * * *

SEQUENCE LISTING

```
<160> NUMBER OF SEQ ID NOS: 37

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(5)
<223> OTHER INFORMATION: Y12XX-hz28 VH-CDR1

<400> SEQUENCE: 1

Ser Tyr Trp Met His
1               5


<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(17)
<223> OTHER INFORMATION: Y12XX-hz28 VH-CDR2

<400> SEQUENCE: 2

Gln Ile Asn Pro Thr Thr Gly Arg Ser Gln Tyr Asn Glu Lys Phe Lys
```

1 5 10 15

Thr

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(8)
<223> OTHER INFORMATION: Y12XX-hz28 VH-CDR3

<400> SEQUENCE: 3

Trp Gly Leu Gln Pro Phe Ala Tyr
1 5

<210> SEQ ID NO 4
<211> LENGTH: 117
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(117)
<223> OTHER INFORMATION: Y12XX-hz28 VH (Vk-hz14)

<400> SEQUENCE: 4

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser
115

<210> SEQ ID NO 5
<211> LENGTH: 446
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(446)
<223> OTHER INFORMATION: HC_Y12XX-hz28-CH1-IgG1-P238K- no terminal lysine

<400> SEQUENCE: 5

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

```
Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 6
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(447)
<223> OTHER INFORMATION: HC_Y12XX-hz28-CH1-IgG1-P238K- with terminal lysine

<400> SEQUENCE: 6

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

```
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 7
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(11)
<223> OTHER INFORMATION: Y12XX-hz28 VL-CDR1

<400> SEQUENCE: 7

Lys Ala Ser Gln Asp Val Ser Thr Ala Val Ala
1               5                   10


<210> SEQ ID NO 8
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(7)
<223> OTHER INFORMATION: Y12XX-hz28 VL-CDR2

<400> SEQUENCE: 8

Ser Ala Ser Tyr Arg Tyr Thr
1               5


<210> SEQ ID NO 9
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(9)
<223> OTHER INFORMATION: Y12XX-hz28 VL-CDR3

<400> SEQUENCE: 9

Gln Gln His Tyr Ser Thr Pro Trp Thr
1               5


<210> SEQ ID NO 10
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
```

<221> NAME/KEY: MISC_FEATURE
<222> LOCATION: (1)..(107)
<223> OTHER INFORMATION: Y12XX-hz28 VL (Vk-hz2)

<400> SEQUENCE: 10

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys
            100                 105
```

<210> SEQ ID NO 11
<211> LENGTH: 214
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(214)
<223> OTHER INFORMATION: LC_Y12XX-hz28 VL CL

<400> SEQUENCE: 11

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 12
<211> LENGTH: 277
<212> TYPE: PRT
<213> ORGANISM: Homo sapiens
<220> FEATURE:
<221> NAME/KEY: MISC_FEATURE
<222> LOCATION: (1)..(277)
<223> OTHER INFORMATION: CD40

<400> SEQUENCE: 12

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275


<210> SEQ ID NO 13
<211> LENGTH: 231
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

<222> LOCATION: (1)..(231)
<223> OTHER INFORMATION: IgG1-P238K (-C-term Lys)

<400> SEQUENCE: 13

Glu Pro Lys Ser Cys Asp Lys Thr His Thr Cys Pro Pro Cys Pro Ala
1 5 10 15

Pro Glu Leu Leu Gly Gly Lys Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 14
<211> LENGTH: 232
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(232)
<223> OTHER INFORMATION: IgG1-P238K

<400> SEQUENCE: 14

Glu Pro Lys Ser Cys Asp Lys Thr His Thr Cys Pro Pro Cys Pro Ala
1 5 10 15

Pro Glu Leu Leu Gly Gly Lys Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 15
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(329)
<223> OTHER INFORMATION: CH1-IgG1-P238K (-C-term Lys)

<400> SEQUENCE: 15

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Lys Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 16
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(330)
<223> OTHER INFORMATION: CH1-IgG1-P238K

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 17
<211> LENGTH: 231
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(231)
<223> OTHER INFORMATION: IgG1f-P238K (-C-term Lys)

<400> SEQUENCE: 17

Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 18
<211> LENGTH: 232
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(232)
<223> OTHER INFORMATION: IgG1f-P238K

<400> SEQUENCE: 18

Glu Pro Lys Ser Cys Asp Lys Thr His Thr Cys Pro Pro Cys Pro Ala
1               5                   10                  15

Pro Glu Leu Leu Gly Gly Lys Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 19
<211> LENGTH: 329
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(329)
<223> OTHER INFORMATION: CH1-IgG1f-P238K (-C-term Lys)

<400> SEQUENCE: 19

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 20
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(330)
<223> OTHER INFORMATION: CH1-IgG1f-P238K

<400> SEQUENCE: 20

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 21
<211> LENGTH: 446
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(446)
<223> OTHER INFORMATION: HC_Y12XX-hz28-CH1-IgG1f-P238K- no terminal
      lysine

<400> SEQUENCE: 21

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Tyr Ala Phe Thr Ser Tyr
            20                  25                  30

Trp Met His Trp Val Arg Gln Ala Pro Gly Gln Gly Leu Glu Trp Met
        35                  40                  45

Gly Gln Ile Asn Pro Thr Thr Gly Arg Ser Gln Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gln Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Lys Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
```

435 440 445

<210> SEQ ID NO 22
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(447)
<223> OTHER INFORMATION: HC_Y12XX-hz28-CH1-IgG1f-P238K- with terminal lysine

<400> SEQUENCE: 22

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Ser Tyr
20 25 30

Trp Met His Trp Val Arg Gln Ala Pro Gly Gln Gly Leu Glu Trp Met
35 40 45

Gly Gln Ile Asn Pro Thr Thr Gly Arg Ser Gln Tyr Asn Glu Lys Phe
50 55 60

Lys Thr Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Trp Gly Leu Gln Pro Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Lys Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

```
Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 23
<211> LENGTH: 98
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(98)
<223> OTHER INFORMATION: heavy chain CH1

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val


<210> SEQ ID NO 24
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(107)
<223> OTHER INFORMATION: light chain CL

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 25

Gly Gly Gly Gly Ser
1               5


<210> SEQ ID NO 26
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 26

Gly Gly Gly Gly Ser Gly Gly Gly Gly Ser
1               5                   10


<210> SEQ ID NO 27
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 27

Gly Gly Gly Gly Ser Gly Gly Gly Gly Ser Gly Gly Gly Gly Ser
1               5                   10                  15


<210> SEQ ID NO 28
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 28

Gly Gly Gly Gly Ser Gly Gly Gly Gly Ser Gly Gly Gly Gly Ser Gly
1               5                   10                  15

Gly Gly Gly Ser
            20


<210> SEQ ID NO 29
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 29

Gly Gly Gly Gly Ser Gly Gly Gly Gly Ser Gly Gly Gly Gly Ser Gly
1               5                   10                  15
```

```
Gly Gly Gly Ser Gly Gly Gly Gly Ser
            20                  25


<210> SEQ ID NO 30
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 30

Ala Ser Thr
1


<210> SEQ ID NO 31
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 31

Thr Val Ala Ala Pro Ser
1               5


<210> SEQ ID NO 32
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 32

Thr Val Ala
1


<210> SEQ ID NO 33
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 33

Ala Ser Thr Ser Gly Pro Ser
1               5


<210> SEQ ID NO 34
<211> LENGTH: 1392
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1392)
<223> OTHER INFORMATION: encodes heavy chain variable domain of
      BMS-986325 including a constant region CH1 and Fc domain
      IgG1-P238K

<400> SEQUENCE: 34

atgagggctt ggatcttctt tctgctctgc ctggccggga gagcgctcgc acaggtgcag      60

ctggtgcagt ctggtgccga ggtcaaaaag ccaggctcca gcgtgaaggt gagctgcaag     120

gcctctggct acgctttcac ctcttattgg atgcactggg tgagacaggc tcctggacag     180

ggcctggagt ggatgggcca gatcaaccca accaccggca gaagccagta caatgagaag     240
```

tttaagaccc gcgtgaccat cacagccgac aagtccacca gcacagctta tatggagctg 300
tcttccctga ggtccgagga tacagccgtg tactattgcg ctcggtgggg cctgcagcct 360
ttcgcttact ggggccaggg caccctggtg acagtgagct ctgctagcac caagggccca 420
tcggtcttcc ccctggcacc ctcctccaag agcacctctg ggggcacagc ggccctgggc 480
tgcctggtca aggactactt ccccgaaccg gtgacggtgt cgtggaactc aggcgccctg 540
accagcggcg tgcacacctt cccggccgtc ctacagtcct caggactcta ctccctcagc 600
agcgtggtga ccgtgccctc cagcagcttg ggcacccaga cctacatctg caacgtgaat 660
cacaagccca gcaacaccaa ggtggacaag agagttgagc ccaaatcttg tgacaaaact 720
cacacatgcc caccgtgccc agcacctgaa ctcctggggg gaaagtcagt cttcctcttc 780
cccccaaaac ccaaggacac cctcatgatc tcccggaccc ctgaggtcac atgcgtggtg 840
gtggacgtga gccacgaaga ccctgaggtc aagttcaact ggtacgtgga cggcgtggag 900
gtgcataatg ccaagacaaa gccgcgggag gagcagtaca acagcacgta ccgtgtggtc 960
agcgtcctca ccgtcctgca ccaggactgg ctgaatggca aggagtacaa gtgcaaggtc 1020
tccaacaaag ccctcccagc ccccatcgag aaaaccatct ccaaagccaa agggcagccc 1080
cgagaaccac aggtgtacac cctgccccca tcccgggatg agctgaccaa gaaccaggtc 1140
agcctgacct gcctggtcaa aggcttctat cccagcgaca tcgccgtgga gtgggagagc 1200
aatgggcagc cggagaacaa ctacaagacc acgcctcccg tgctggactc cgacggctcc 1260
ttcttcctct acagcaagct caccgtggac aagagcaggt ggcagcaggg gaacgtcttc 1320
tcatgctccg tgatgcatga ggctctgcac aaccactaca cgcagaagag cctctccctg 1380
tctccgggtt ga 1392

<210> SEQ ID NO 35
<211> LENGTH: 696
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(696)
<223> OTHER INFORMATION: encodes the light chain variable domain of BMS-986325 including a constant region CL

<400> SEQUENCE: 35
atgagggctt ggatcttctt tctgctctgc ctggccgggc gcgccttggc cgacatccag 60
atgacccagt ccccctcctt cctgtctgcc tccgtgggcg acagagtgac catcacctgt 120
aaggcttccc aggatgtgag cacagccgtg gcttggtacc agcagaagcc aggcaaggcc 180
cccaagctgc tgatctattc cgcctcttac aggtataccg gcgtgccctc tcggttctcc 240
ggcagcggct ctggcacaga ctttaccctg acaatctcca gcctgcagcc tgaggatttc 300
gccacctact attgccagca gcactactcc accccatgga catttggcgg cggcaccaag 360
gtggagatca agcgtacggt ggctgcacca tctgtcttca tcttcccgcc atctgatgag 420
cagttgaaat ctggaactgc ctctgttgtg tgcctgctga ataacttcta tcccagagag 480
gccaaagtac agtggaaggt ggataacgcc ctccaatcgg gtaactccca ggagagtgtc 540
acagagcagg acagcaagga cagcacctac agcctcagca gcaccctgac gctgagcaaa 600
gcagactacg agaaacacaa agtctacgcc tgcgaagtca cccatcaggg cctgagctcg 660
cccgtcacaa agagcttcaa caggggagag tgttag 696

```
<210> SEQ ID NO 36
<211> LENGTH: 17
<212> TYPE: PRT
<213> ORGANISM: Artificial Sequence
<220> FEATURE:
<223> OTHER INFORMATION: Signal peptide

<400> SEQUENCE: 36

Met Arg Ala Trp Ile Phe Phe Leu Leu Cys Leu Ala Gly Arg Ala Leu
1               5                   10                  15

Ala


<210> SEQ ID NO 37
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(51)
<223> OTHER INFORMATION: encodes signal peptide

<400> SEQUENCE: 37

atgagggctt ggatcttctt tctgctctgc ctggccggga gagcgctcgc a             51
```